(12) United States Patent
Desprez et al.

(10) Patent No.: US 7,429,457 B2
(45) Date of Patent: Sep. 30, 2008

(54) ID-1 AND ID-2 GENES AND PRODUCTS AS MARKERS OF EPITHELIAL CANCER

(75) Inventors: Pierre-Yves Desprez, El Cerrito, CA (US); Judith Campisi, Berkeley, CA (US)

(73) Assignees: The Regents of the University of California, Oakland, CA (US); California Pacific Medical Center, San Francisco, CA (US)

( * ) Notice: Subject to any disclaimer, the term of this patent is extended or adjusted under 35 U.S.C. 154(b) by 0 days.

(21) Appl. No.: 09/952,534

(22) Filed: Sep. 14, 2001

(65) Prior Publication Data

US 2002/0137064 A1    Sep. 26, 2002

Related U.S. Application Data

(60) Provisional application No. 60/232,529, filed on Sep. 14, 2000, provisional application No. 60/232,558, filed on Sep. 14, 2000.

(51) Int. Cl.
*G01N 33/53* (2006.01)

(52) U.S. Cl. .................. 435/7.1; 435/7.23; 435/7.9; 530/350; 530/387.1

(58) Field of Classification Search .............. 435/7.1, 435/7.23, 7.9; 530/350, 387.1
See application file for complete search history.

(56) References Cited

U.S. PATENT DOCUMENTS 6,048,850 A    4/2000    Young et al. ............... 514/183

OTHER PUBLICATIONS

Vandesompele J et al, 2003, Oncogene, 22(3): 456-60.*
Maruyama, H et al, 1999, Amer J Pathol, 155(3) : 815-22.*
Stewart, HJ et al, 1997, J Neurosci res,50(5): 684-701.*
Hsu (in Tissue Culture Methods and Applications, Kruse and Patterson, Eds, 1973, Academic Press, NY, see abstract, p. 764).*
Freshney (Culture of Animal Cells, A Manual of Basic Technique, Alan R. Liss, Inc., 1983, New York, p4).*
Dermer (Bio/Technology, 1994, 12:320).*
Morrow MA et al, Mol Immunol, 1999, 36(8): 491-503.*
Oesterreich, S et al, 1996, Clin Cancer Res, 2: 1199-1206.*
Tockman et al (Cancer Res., 1992, 52:2711s-2718s).*
Drexler et al (Leukemia and Lymphoma, 1993, 9:1-25).*
Embleton et al. (Immunol Ser, 1984, 23:181-207).*
Ausubel, FM, et al, eds, 1987, Current protocols in Molecular Biology, John Wiley & Sons, p. 6.3.5.*
Schmid S et al, 2001, J comparative Neurology, 430(2): 160-71.*
Conner et al, 1996, Mol Brain Res, 42: 1-17.*
Bowie et al (Science, 1990, 257 : 1306-1310).*
Burgess et al, (Journal of Cell Biology, 1990, 11: 2129-2138).*
Lazar et al. Molecular and Cell Biology, 1988, 8: 1247-1252.*
Tao. et al. The Journal of Immunology, 1989, 143(8): 2595-2601.*
Gillies et al. Human Antibodies and Hybridomas, 1990, 1(1): 47-54).*
Schmid S et al, 2001 (J comparative Neurology, 430(2): 160-71).*
Conner et al, 1996 (Mol Brain Res, 42: 1-17).*
Kenneth Langlands, et al., Id Proteins Are Dynamically Expressed in Normal Epidermis and Dysregulated in Squamous Cell Carcinoma, *Cancer Research*, 60:5929-5933 (Nov. 1, 2000).
Robert Benezra, The Id Proteins: Targets for Inhibiting Tumor Cells and Their Blood Supply, *Biochimica et Biophysica Acta*, 1551:F39-F47, (2001).
Claudia Qiao Lin, et al., A Role for Id-1 In the Aggressive Phenotype and Steroid Hormone Response of Human Breast Cancer Cells, *Cancer Research*, 60:1332-1340 (Mar. 1, 2000).
Yong Liu, et al., Systemic Gene Delivery Expands the Repertoire of Effective Antiangiogenic Agents, The Journal of Biological Chemistry, 274/19:13338-13344, (May 7, 1999).
Takai et al., "Id1 expression is associated with histological grade and invasive behavior in endometrial carcinoma," Cancer Letters, Elsvier Science Ireland Ltd., vol. 165, p. 185-193, (2001).
Schindl et al., "Overexpression of Id-1 Protein is a Marker for Unfavorable Prognosis in Early-Stage Cervical Cancer," Cancer Research, vol. 165, p. 5703-5706, (Aug. 1, 2001).
Schindl et al., "Level of Id-1 Protein Expression Correlates with Poor Differentiation, Enhanced Malignant Potential, and More Agressive Clinical Behavior of Epithelial Ovarian Tumors," Clinical Cancer Research, vol. 9, p. 779-785, (Feb. 2003).
Schoppmann et al., "Overexpression of Id-1 is associated with Poor Clinical Outcome in Node Negative Breast Cancer," Int. J. Cancer, 2003 Wiley-Liss, Inc., vol. 104, p. 677-682, (2003).

* cited by examiner

*Primary Examiner*—Larry R. Helms
*Assistant Examiner*—Minh-Tam Davis
(74) *Attorney, Agent, or Firm*—Michelle Chew Wong; Lawrence Berkeley National Laboratory

(57) ABSTRACT

A method for detection and prognosis of breast cancer and other types of cancer. The method comprises detecting expression, if any, for both an Id-1 and an Id-2 genes, or the ratio thereof, of gene products in samples of breast tissue obtained from a patient. When expressed, Id-1 gene is a prognostic indicator that breast cancer cells are invasive and metastatic, whereas Id-2 gene is a prognostic indicator that breast cancer cells are localized and noninvasive in the breast tissue.

5 Claims, 12 Drawing Sheets

1: MDA-MB436 CONTROL
2: MDA-MB436 Id1 SENSE
3: MDA-MB436 Id1 AS

Figure 16(a)

Friday, September 15, 2000                         NCBI Sequence Viewer

NCBI Nucleotide

Search [Nucleotide ▼] for [_____] [Go] [Clear]
        Limits    Index    History    Clipboard
[Display] [Default ▼] View as [HTML ▼] [Save] [Add to Clipboard]  ☐ Hide Brief and LinkBar ☐ 1: GI = "457784" [GenBank]  H.sapiens Id1 mRNA    PubMed, Protein, Related Sequences, Taxonomy, OMIM, LinkOut

```
LOCUS       HSID1      926 bp    mRNA          PRI    19-JAN-1995
DEFINITION  H.sapiens Id1 mRNA.
ACCESSION   X77956
VERSION     X77956.1  GI:457784
KEYWORDS    Id1 gene.
SOURCE      human.
  ORGANISM  Homo sapiens
            Eukaryota; Metazoa; Chordata; Vertebrata; Mammalia; Eutheria;
            Primates; Catarrhini; Hominidae; Homo.
REFERENCE   1  (bases 1 to 926)
  AUTHORS   Deed,R.W., Jasiok,M. and Norton,J.D.
  TITLE     Nucleotide sequence of the cDNA encoding human helix-loop-helix
            Id-1 protein: identification of functionally conserved residues
            common to Id proteins
  JOURNAL   Biochim. Biophys. Acta 1219 (1), 160-162 (1994)
  MEDLINE   94368847
REFERENCE   2  (bases 1 to 926)
  AUTHORS   Deed,R.
  TITLE     Direct Submission
  JOURNAL   Submitted (25-FEB-1994) R. Deed, Paterson Institute for Cancer
            Research, Dept of Regulation, Christie Hospital NHS Trust, Wilmslow
            Road, Manchester, UK
FEATURES             Location/Qualifiers
     source          1..926
                     /organism="Homo sapiens"
                     /db_xref="taxon:9606"
                     /clone="Id1"
                     /tissue_type="placenta"
                     /clone_lib="lambda gt10"
                     /germline
     gene            36..500
                     /gene="Id1"
     CDS             36..500
                     /gene="Id1"
                     /codon_start=1
                     /protein_id="CAA54920.1"
                     /db_xref="GI:457785"
                     /db_xref="SWISS-PROT:P41134"
                     /translation="MKVASGSTATAAAGPSCALKAGKTASGAGEVVRCLSEQSVAISR
                     CRGAGARLPALLDEQQVNVLLYDMNGCYSRLKELVPTLPQNRKVSKVEILQHVIDYIR
                     DLQLELNSESEVGTPGGRGLPVRAPLSTLNGEISALTAEAACVPADDRILCR"
     polyA_signal    893..898
BASE COUNT      193 a    262 c    281 g    190 t
ORIGIN
        1 ggggcccatt ctgttcagc cagtcgccaa caatcatgaa agtcgccagt ggcagcaccg
       61 ccaccgccgc cgcgggcccc agctgcgcgc tgaaggccgg caagacacg agcggtgcgg
      121 gcgaggtggt gcgctgtctg tctgagcaga gcgtggccat ctcgcgctgc cgggcgccg
      181 gggcgcgcct gccdgccctg ctggacgagc agcaggtaaa cgtgctgctc tacgacatga
      241 acggctgtta cteacgcctc aaggagctgg tgcccaccct gccccagaac cgcaaggtga
      301 gcaaggtgga gattctccag cacgtcatcg actacatcag ggaccttcag ttggagctga
      361 actcggaalc cgaagttggg accccgggg gccgagggct gccggtccgg gctccgctca
      421 gcacccctcaa cggcgagatc agcgccctga cggccgaggc ggcatgcgtt cctgccgacg
      481 atcgcatctt gtgtcgctga agcgcctccc ccagggaccg gcggaccca gccatccagg
      541 gggcaagagg aattacgtgc tctgtgggtc tccccaacg cgcctcgccg gatctgaggg
      601 agaacaagac cgatcggcgg ccactgcgcc cttaactgca tccagcctgg ggctgaggct
      661 paggcactgg cgaggagagg gcgctcctct ctgcacaccct actagtcacc agagacttta
      721 gggggtggga ttccactcgt gtgttctat tttgaaaa gcagacattt taaaaatgg
      781 tcacgttgg tgcttctcag attctgagg aaattgcttt gtattgtata ttacaatgat
```

FIGURE 16(b)

Friday, September 15, 2000                                                                 NCBI Sequence Viewer 841 caccgactga gaatattgtt ttacaatagt tctgtggggc tgtttttttg ttattaaaca
901 aataatttag atggtgaaaa aaaaaa

Figure 17 (a)

Friday, September 15, 2000                                          NCBI Sequence Viewer

Search [Nucleotide ▼] for [                              ] [Go] [Clear]
              Limits        Index        History      Clipboard
[Display] [Default ▼] View as [HTML ▼] [Save] [Add to Clipboard] ☐ Hide Brief and LinkBar ☐ 1: GI = "464183" [GenBank] Human mRNA for Id-2H, compl... PubMed, Protein, Related Sequences, Taxonomy, OMIM, Lin

```
LOCUS       HUMID2HC    1049 bp    mRNA         PRI    03-FEB-1999
DEFINITION  Human mRNA for Id-2H, complete cds.
ACCESSION   D13891
VERSION     D13891.1  GI 464183
KEYWORDS    Id-2H; Id-related gene; cell cycle dependent gene; helix-loop-helix
            protein.
SOURCE      Homo sapiens lung fibroblasts (haplotype diploid) cell-line TIG-3
            cDNA to mRNA.
  ORGANISM  Homo sapiens
            Eukaryota; Metazoa; Chordata; Vertebrata; Mammalia; Eutheria;
            Primates; Catarrhini; Hominidae; Homo.
REFERENCE   1  (bases 1 to 1049)
  AUTHORS   Hara,E.
  TITLE     Direct Submission
  JOURNAL   Submitted (07-DEC-1992) to the DDBJ/EMBL/GenBank databases. Eji
            Hara, Science University of Tokyo, Dept. of Biol. Science &
            Technol.; 2641 Yamazaki, Noda-shi, Chiba 278, Japan
            (Tel:0471-24-1501(ex.4421), Fax:0471-25-1841)
REFERENCE   2  (bases 1 to 1049)
  AUTHORS   Hara,E., Yamaguchi,T., Nojima,H., Ide,T., Campisi,J., Okayama,H.
            and Oda,K.
  TITLE     Id-related genes encoding helix-loop-helix proteins are required
            for G1 progression and are repressed in senescent human fibroblasts
  JOURNAL   J. Biol. Chem. 269 (3), 2139-2145 (1994)
  MEDLINE   94124570
COMMENT     Submitted (07-Dec-1992) to DDBJ by:
            Eji Hara
            Dept. of Biological Science
            & Technology
            Scienci University of Tokyo
            2641 Yamazaki Noda-shi
            Chiba 278
            Japan
            Phone: 0471-24-1501 x4421
            Fax:   0471-25-1841
FEATURES             Location/Qualifiers
     source          1..1049
                     /organism="Homo sapiens"
                     /db_xref="taxon:9606"
                     /haplotype="diploid"
                     /cell_line="TIG-3"
                     /cell_type="fibroblasts"
                     /tissue_type="lung"
     gene            97..501
                     /gene="Id-2H"
     CDS             97..501
                     /gene="Id-2H"
                     /codon_start=1
                     /product="Id-2H"
                     /protein_id="BAA02990.1"
                     /db_xref="GI:471126"
                     /translation="MKAFSPVRSVRKNSLSDHSLGISRSKTPVDDPMSLLYNMNDCYS
                     KLKELVPSIPQNKKVSKMEILQHVIDYILDLQIALDSHPTIVSLHHQRPGQNQASRTP
                     LTTLNTDISILSLQASEFPSELMSNDSKALCG"
BASE COUNT      298 a   258 c   222 g   271 t
ORIGIN
        1 gcccggtgcc aagcgcagct agctcagcag gcggcagcgg cggcctgagc ttcagggcag
       61 ccagctcctc ccggtctcgc ctccctcgcg gtcagcatga aagccttcag tcccgtgagg
```

Figure 17 (b)

Friday, September 15, 2000                                           NCBI Sequence Viewer

```
 121 tccgttagga aaaacagcct gtcggaccac agcctgggca tctcccggag caaaaccoct
 181 gtggacgacc cgatgagcct gctatacaac atgaacgact gctactccaa gctcaaggag
 241 ctggtgccca gcatccccca gaacaagaag gtgagcaaga tggaaatcct gcagcacgtc
 301 atcgactaca tcttggacct gcagatcgcc ctggactcgc atcccactat tgtcagcctg
 361 catcaccaga gacccgggca gaaccaggcg tccaggacgc cgctgaccac cctcaacacg
 421 gatatcagca tcctgtcctt gcaggcttct gaattcccct ctgagttaat gtcaaatgac
 481 agcaaagcac tgtgtggctg aataagcggt gttcatgatt tctttattc tttgcacaac
 541 aacaacaaca acaaattcac ggaatctttt aagtgctgaa cttattttc aaccattca
 601 caaggaggac aagttgaatg gacctttta aaaagaaaaa aaaaatgaag gaaaactaag
 661 aatgatcatc ttcccagggt tcttacttga ctgtaattcg ttatttatga aaaaacccttt
 721 taaatgccct ttctgcagtt ggaaggtttt ctttatatac tattcccacc atgggagcg
 781 aaaacgttaa aatcacaagg aattgcccaa tctaagcaga cttttgcctt tttcaaaggt
 841 ggagcgtgat accagaagga tccagtattc agtcacttaa atgaagtctt ttggtcagaa
 901 attaccttt tcacacaagc ctactgaatg ctgtgtatat attlatatat aaatatatct
 961 attgagtga aaccttgtga accttlaatt agagtcttct tgtatagtgg cagagatgtc
1021 tattctgcat caaagtgtaa tgatgtact
```

ID-1 AND ID-2 GENES AND PRODUCTS AS MARKERS OF EPITHELIAL CANCER

This application is based on and claims priority of the Provisional application Ser. Nos.: 60/232,529 and 60/232,558, both filed on Sep. 14, 2000.

This invention was made with government support under Contract No. DE-AC03-76SF00098, awarded by the United States Department of Energy, and under NIH Grant for NCI RO1CA82548. The Government has certain rights in this invention.

BACKGROUND OF THE INVENTION

1. Field of the Invention

The present invention concerns a diagnosis, prognosis and treatment of breast, endometrium, cervical, ovarian, squamous cell, prostate and melanoma cancer. Particularly, the invention concerns the use of Id-1 and/or Id-2 genes or Id-1 and/or Id-2 products as diagnostic markers for cancer cells metastatic aggressivity and use of detection of the Id-1 or Id-2 genes, or a ratio thereof, or use of detection of the Id-1 or Id-2 products, or a ratio thereof, for diagnosis and prognosis of breast cancer. The invention further concerns a method for treatment of breast cancer by targeting Id-1 or Id-2 genes, or a combination thereof, through delivery of antisense transcripts, ribozymes, small therapeutically active molecules, drugs, peptides or organic compounds that disrupt Id-1 protein interaction with bHLH transcription factor or enhance Id-2 action with bHLH transcription factor and vice versa, RNA, anti-Id-1 RNAi causing degradation of homologous Id-1 mRNAs, Id-2 as a gene or a protein, or ITF-2 as a gene or protein, or targeting Id-1 or Id-2 proteins with antibodies or with compounds which either enhance or impair their expression thereby affecting the feedback of the gene expression. The invention further concerns the detection of Id-1 or Id-2 products or genes or their ratio with a kit comprising anti Id-1 and/or Id-2 antibodies or Id-1 or Id-2 probes.

2. Description of Related Art

Breast cancer is one of the most common malignancies among women and shares, together with lung carcinoma, the highest fatality rate of all cancers affecting females.

There are very few diagnostic markers available for breast cancer detection and those which are available have a predictive accuracy only about twenty percent. There is no marker available that can detect or determine cancer cells metastatic aggressivity.

The current treatment of the breast cancer is limited to a very invasive, total or partial mastectomy, radiation therapy, or chemotherapy, later two resulting in serious undesirable side effects.

It would thus be desirable to have available additional new diagnostic methods which would detect the presence of cancer with greater accuracy and which would permit determination of distinction of highly aggressive breast cancer cells having a tendency to metastasize from the cancer cells which remain localized and have low probability of metastatic spread. It would also be desirable to have available methods for less invasive treatment of the breast or other cancers.

The mammary gland is one of the few organs that undergo striking morphological and functional changes during adult life, particularly during pregnancy, lactation, and involution.

When normal epithelial breast cells become transformed, a number of genetic alterations affect growth control, maintenance of differentiated epithelial functions and invasiveness. Identifying the genes involved in these processes is essential for understanding how breast cancer develops, and for deriving better methods for prognosis and treatment.

In both humans and mice, fetal virgin adult, and pregnant mammary glands undergo extensive temporal, structural and spatial remodeling, which entails invasion, migration, and relocation of cells to generate the ductal and alveolar structures of the gland. Once lactation is terminated, there is additional and extensive tissue remodeling as the gland returns to its resting state.

During each menstrual cycle, and especially during pregnancy, lactation and involution, mammary epithelial cells go through cycles of proliferation, invasion, differentiation and apoptotic cell-death. The mechanisms that regulate these complex and developmentally coordinated cell phenotypes are only poorly understood. However, at least some of the downstream genes that are regulated during these different stages of mammary development have been identified.

In recent years, some progress has been also made in elucidating the mechanisms that regulate mammary gland-specific gene expression and the transformation of mammary epithelial cells to malignancy. However, the practical use of these findings for detection, prognosis and treatment of cancer and its malignant propensities has not been described.

It is, therefore, a primary objective of this invention to provide a method and means for detection and prognosis of breast cancer, for determination of the malignant aggressivity of cancer cells and for providing therapeutically effective agents for suppression and therapy of breast, endometrium, cervical, ovarian, squamous cells and prostate cancer and melanoma.

All patents, patent applications and publications cited herein are hereby incorporated by reference.

SUMMARY OF THE INVENTION

One aspect of the current invention is a method for diagnosis, prognosis and treatment of breast, cervical, ovarian, endometrium, squamous, prostate and melanoma cancer.

Another aspect of the current invention is the use of Id-1 and/or Id-2 genes as diagnostic markers for metastatic aggressivity of breast, cervical, ovarian, endometrium and squamous cancer cells.

Yet another aspect of the current invention is the use of Id-1 and/or Id-2 proteins as diagnostic markers for metastatic aggressivity of prostate and melanoma cancer cells.

Still another aspect of the current invention is a method for detection of the Id-1 or Id-2 genes, or a ratio thereof, or for detection of the Id-1 or Id-2 products, or a ratio thereof, as the markers for diagnosis and prognosis of breast cancer.

Still yet another aspect of the current invention is a method for treatment of breast cancer and other types of cancer by targeting Id-1 and/or Id-2 genes, or a combination thereof, through a delivery of antisense transcripts, ribozymes, small therapeutically active molecules, drugs, peptides or organic compounds that disrupt Id-1 interaction with a bHLH transcription factor or enhance Id-2 protein action with a bHLH transcription factor, RNA, anti-Id-1 RNAi causing degradation of homologous Id-1 mRNAs, Id-2 as a gene or a protein, or ITF-2 gene or protein.

Yet another aspect of the current invention is a kit for detection of Id-1 or Id-2 genes or Id-1 or Id-2 products, or their ratio, said kit comprising anti Id-1 and/or Id-2 antibodies or anti Id-1 and/or Id-1 probes.

BRIEF DESCRIPTION OF THE DRAWINGS

FIG. 16 (a-b) is a print out from the NCBI, and sets forth Accession No. X77956 (definition, "Homo sapiens Id-1 mRNA"), and provides *H. sapiens* Id-I gene (SEQ ID. No. 1) and Id-1 protein (SEQ ID. No. 2) encoded thereby.

FIG. 17 (a-b) is a print out from the NCBI, and sets forth Accession No. D13891 (definition, "Human mRNA for Id-2H, complete cds"), and provides *H. sapiens* Id-2 gene SEQ ID. No. 3) and Id-2 protein (SEQ ID. No. 4) encoded thereby.

DEFINITIONS

Figure 1:
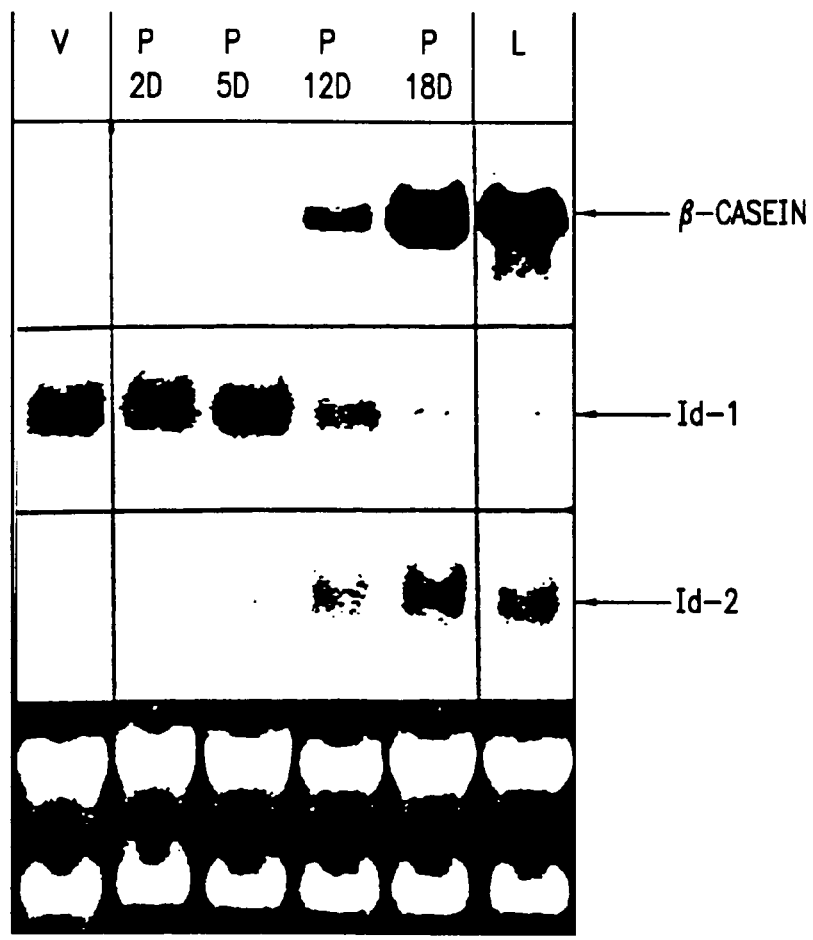
FIG. 1 is a Northern blot showing a pattern of Id-1 and Id-2 expression in the mouse mammary gland.

As used herein:

"Id" means inhibition of differentiation or DNA binding.

"Id proteins" means proteins which are inhibitors of differentiation or DNA binding. Since Id proteins function by binding basic helix-loop-helix (bHLH) transcription factors, Id-1- or Id-2-interacting proteins are important transcriptional regulators of mammary epithelial cell properties.

"Id-1" means protein expressed by Id-1 gene. High levels of Id-1 protein are expressed by aggressive and metastatic breast, cervical, ovarian, endometrium and squamous cancer cells. High levels of Id-1 protein are expressed in noninvasive prostate cancer and melanoma.

"Id-2" means protein expressed by Id-2 gene. Increased levels of Id-2 protein are crucial for normal breast development. Breast, cervical, endometrium and squamous cancer cells producing high level of Id-2 protein are less invasive. Increased levels of Id-2 protein are expressed by highly invasive and metastatic prostate cancer cells.

"Id-1-interacting proteins" are proteins which interact with Id-1 protein. These proteins are, therefore, important transcriptional regulators of mammary epithelial cell properties.

"ITF-2" is a bHLH transcription factor which interacts with Id-1 and is, therefore, an example of Id-1 interacting protein. ITF-2 appears to be constitutively expressed in SCp2 epithelial cells. Although Id-1 expression fluctuates during mammary epithelial cell growth and differentiation, the expression of ITF-2, determined by ITF-2 mRNA, in such proliferating and differentiating SCp2 cells, does not fluctuate. The mouse ITF-2 (mITF-2) insert was found to contain a 950 bp open reading frame encoding the bHLH and C-terminal domains of ITF-2, but missing the N-terminal region.

"HLH" means helix-loop-helix.

"bHLH" means basic helix-loop-helix.

"GAPDH" means glyceraldehyde-3-phosphate dehydrogenase.

"DAPI" means 4', 6-diamidino-2-phenylindole.

"DCIS" means ductal carcinoma in situ.

"EGR" means early growth.

"Gene product" means a protein or mRNA.

"RNAi" means RNA interference process for a sequence-specific post-transcriptional gene silencing of a gene by providing a double-stranded RNA (dsRNA) that is homologous in sequence to the silenced gene. Small interfering RNAs (siRNAs) generated by ribonuclease III cleavage from longer dsRNA are the mediators of sequence-specific mRNA degradation.

DETAILED DESCRIPTION OF THE INVENTION

The current invention is based on findings that Id-1 and Id-2 genes are involved in tumor progression of breast, cervical, ovarian, endometrium, squamous cells and prostate carcinoma and melanoma and that Id-1 and Id-2 genes are involved in the development of breast cancer and are, therefore, suitable to serve as diagnostic markers and therapeutic targets for these types of cancer.

Specifically, it has been discovered that Id-1 gene is involved in and plays a critical role in the development of a proliferative and invasive phenotype in breast, cervical, endometrium and squamous epithelial cells and that it is constitutively expressed in the least differentiated and highly aggressive human cancer cells and that Id-2 gene is involved in development of a less aggressive or non-aggressive phenotype in these cancer cells.

The Id-2 gene, on the other hand is involved in the development of a proliferative and invasive phenotype in prostate cancer cells, where Id-1 gene seems to play just the opposite role, that is, it is involved in the development of a less aggressive or nonaggressive phenotype and prostate and melanoma cancer cells.

It has been further discovered that both Id-1 and Id-2 genes, Id-1 and Id-2 proteins, and their respective ratios, may be conveniently detected.

Additionally, the invention is based on findings that both Id-1 and Id-2 genes expression may be effectively suppressed or at least decreased by the targeted conversion with amphotropic retrovirus carrying Id-1 or Id-2 antisense.

Consequently, the invention concerns, in its broadest scope, a diagnosis, prognosis and treatment of breast, endometrial, cervical, ovarian, squamous cells or prostate carcinoma or melanoma.

I. Function of Id-1 and Id-2 Genes and Breast Cancer

Aggressive breast cancer cells that are metastasizing to other parts of the body have been known to loose a specific regulation of the gene involved in normal breast cell development. By contrast, normally developing breast cells maintain this regulation. Little is known, however, about the transcriptional regulators that control the expression of these developmental stage-specific genes.

Basic helix-loop-helix (bHLH) transcription factors are key regulators of lineage- and tissue-specific gene expression in a number of mammalian and non-mammalian organisms. These transcription factors bind DNA as homo- or heterodimers, and activate the transcription of target genes containing E-boxes or E-box-like sequences in their promoters. Dimerization occurs through the HLH domains, whereas DNA binding occurs through the two basic domains.

Id proteins, which are inhibitors of differentiation or DNA binding, are helix-loop-helix (HLH) proteins that lack a basic domain. Id proteins act as dominant inhibitors of bHLH transcription factors by forming transcriptionally inactive heterodimers.

So far, four Id genes (Id-1 through Id-4) have been identified. These genes, although similar in their organization and HLH sequences, localize to different chromosomes and show differences in their pattern of expression and function. For example, the cytogenetic location of Id-1 protein is 20q11, whereas location of Id-2 is 2p25, location of Id-3 is 1p36.13-p36.12 and location of Id-4 is 6p22-p21.

The helix-loop-helix protein Id-1 has been shown to inhibit the activity of basic helix-loop-helix transcription factors, and is an important regulator of cell growth and tissue-specific differentiation.

These findings led inventors to investigate a possible correlation between the levels of Id-1 protein and the aggressiveness of human breast cancer cells leading to the current discovery.

A. Id-1 and Id-2 Gene DNA Sequences

Nucleotide sequences of human Id-1 and Id-2 genes are known and have been deposited at GenBank under Accession numbers D13891 and X77956, respectively. Nucleotide sequence which is a source for Id-1 gene comprises of 926 nucleotides with an Id-1 gene encoding region starting at nucleotide 36 and ending at nucleotide 500. Nucleotide sequence which is a source for Id-2 gene comprises of 1049 nucleotides with Id-2 gene coding region starting at nucleotide 97 and ending at nucleotide 501.

B. Function of Id-1 and Id-2 Genes

It has been now discovered that Id-1 and Id-2 genes function as negative regulators of helix-loop-helix (bHLH) transcription factors playing a critical role in the development of a proliferative and invasive phenotype. Such function of Id-1 and Id-2 genes was not previously known.

During the development of the current invention the ectopic expression of the Id-1 gene has been found to inhibit differentiation and stimulate the proliferation and invasiveness of mammary epithelial cells.

The expression of Id-2 gene, on the other hand, has been found to be up-regulated during differentiation of mammary epithelial cells and its expression increased in the differentiated human breast cancer cells. Such up-regulation of Id-2 expression was found to be a necessary step toward a fully differentiated phenotype in breast cells.

Compared to expression of Id-1, expression of Id-2 was found to be much higher in the differentiated human breast cells than the expression of the very aggressive and metastatic cells leading to conclusion that there may be a correlation between the levels of Id-1 or Id-2 proteins and the aggressiveness or non-aggressiveness in human breast cancer cells.

The Id-1 and Id-2 protein levels change dramatically at different stages of breast development. An increase in the level of Id-2 protein is crucial for normal breast development. In breast cancer cells, the cancer cells producing high levels of Id-2 protein are less invasive. By contrast, aggressive and metastatic breast cancer cells express high level of Id-1 mRNA and Id-1 protein.

C. Experimental Evidence and Studies

The evidence supporting the above described findings is based on studies performed on murine epithelial cell lines, on normal mouse mammary glands in vivo, on human breast cancer cells and on human breast cancer biopsies.

1. Effect of Manipulating Id-1 Expression on Differentiation of Murine Mammary Epithelial SCp2 Cell Phenotypes SCp2 cells, a cell line developed from murine mammary gland, are a useful model system for studying mammary epithelial cell growth and differentiation in cell culture.

A role of Id genes in the normal differentiation of SCp2 cells was first suggested by inventors prior findings that Id-1 expression declined rapidly to undetectable levels when the cells differentiated in response to lactogenic hormones, such as insulin, prolactin and hydrocortisone and upon contact with basement membrane (*Mol. Cell Biol.*, 15:3398-3404 (1995).

To directly test the role of Id-1 in these cells, the cells were transfected with an expressible murine Id-1 gene, in either the sense or antisense orientation.

In monolayer culture and low serum medium, Id-1 sense cells grew faster than control cells transfected with the vector lacking a cDNA insert. By contrast, Id-1 antisense cells grew more slowly than controls. Both Id-1 sense and Id-1 antisense cells ceased growth and formed aggregates or spheres when provided with basement membrane and lactogenic hormones. However, Id-1 sense cells formed spheres that were less compact than spheres formed by controls or antisense expressing cells, and failed to express the milk protein β-casein. Under the same conditions, Id-1 antisense cells expressed β-casein at a higher level than control cells.

Despite differences in β-casein expression, control, Id-1 sense and Id-1 antisense cells exposed to hormones and basement membrane remained a growth arrested for 5 to 6 days.

After 8-10 days, however, spheres of Id-1 sense cells began to disintegrate as individual cells dissociated from the sphere, began to invade the basement membrane and resumed growth. In the Boyden Chamber invasion assay, Id-1 sense cells were much more invasive than normal SCp2 or Id-1 antisense cells. The Id-1 sense cells, unlike control or Id-1 antisense cells, expressed a gelatinase of approximately 120 kDa. The activity of this gelatinase was specifically inhibited by inhibitors of matrix-metalloproteinases.

Id-1 protein expression in the nontransformed SCp2 cells resulted in a loss of cell-cell interaction, loss of ability to express markers of differentiation and in an increased ability to invade a basement membrane, migrate and proliferate.

All these propensities make the cells expressing constitutively high levels of Id-1 protein most highly aggressive and metastatic.

2. The Role of Id-1 in Normal Mammary Gland Development In Vivo

The role of Id-1 in normal mammary gland was determined by following the expression of Id-1 during normal mouse mammary gland development in vivo, using Northern analysis of total RNA from virgin (V), pregnant (P; days 2 to 18), and lactating (L) mice. Result are shown in FIG. 1.

FIG. 1 is a Northern analysis of total RNA extracted from mouse mammary gland at different stages of development. Northern analysis utilized cDNA probes for mouse β-casein, Id-1 and Id-2 gene expression.

As seen in FIG. 1, β-casein mRNA was evident only during mid and late pregnancy and lactation. When the blot was reprobed with Id-1 cDNA, Id-1 expression was found to be inversely correlated with β-casein expression, confirming the role of Id-1 gene in vivo observed in the SCp2 cells.

These results clearly show that Id-1 expression declines when the mammary gland proceeds toward full differentiation during pregnancy and at the lactation stage. Id-1 thus is expressed primarily in cells which are nondifferentiated or begin to differentiate.

3. Analysis of Id-1 Expression in Human Breast Cancer Cell Lines and Breast Biopsies Findings that ectopic Id-1 expression induced an invasive phenotype in mouse mammary epithelial cells suggested that Id-1 gene could contribute to human breast cancer progression.

To begin to explore this possibility, human breast cancer cell lines exhibiting varying degrees of invasiveness in culture and in vivo, using metastatic tumor formation in nude mice, was examined. Results of these studies show that highly aggressive human breast cells have lost their serum regulation of Id-1 gene expression. Results are shown in FIGS. 2-6.

The regulation of Id-1 gene expression in the presence of serum was examined in non-invasive cancer T47D and MCF-7 cell lines and in aggressive and invasive cancer MDA-MB-231 and MDA-MB-435 cell lines. The first two are non-invasive human breast cancer cell lines, the latter two are highly invasive metastatic cells which were selected for a highly aggressive phenotype by passage in immunodeficient mice. All cells were purchased from the American Tissue Culture Collection (ATCC).

In some cells, Id-1 gene expression is known to be induced by certain mitogens, such as, for example, serum. Consequently, the effect of the presence or absence of serum on expression of Id-1 gene in these two types of cells was investigated. RNA was isolated from both types of cells that were grown on either 10% serum (G) or incubated in serum-free medium (SF). RNA was then analyzed by Northern analysis according to Example 3. Results are seen in FIG. 2.

Figure 2:
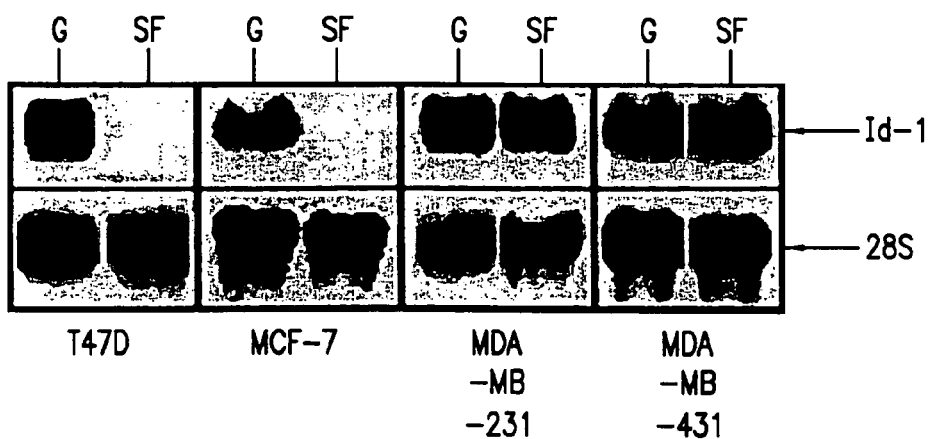
FIG. 2 is a Northern mRNA blot of Id-1 expression in cultured breast cancer cells that were either growing in 10% serum (G) or incubated in serum-free medium (SF).

FIG. 2 illustrates a loss of serum-regulated Id-1 expression in aggressive breast cancer cells. Upper panel shows a position of Id-1 mRNA (1.2 kb). Lower panel shows a position of the ribosomal 28S RNA used as control for RNA integrity and quantitating.

As seen in FIG. 2, T47D and MCF-7 non-invasive cancer cells expressed high levels of Id-1 mRNA only when cultured in serum. When cultured in serum-free medium for two days, such expression levels were undetectable. In contrast, highly aggressive and metastatic MDA-MB-231 and MDA-MB-435 cells constitutively expressed Id-1 mRNA, regardless of the presence or absence of serum.

These results show that in non-invasive breast cancer cell, the expression of Id-1 gene could be induced by culturing these cells in the presence of serum. However, in these non-invasive breast cancer cells, this gene was not expressed and the expression could not be induced in serum-free medium. On the contrary, the invasive metastatic cancer cells expressed Id-1 gene in both the serum containing and serum-free medium. Consequently, the invasive metastatic breast cancer cells do not need Id-1 expression induction by serum but it is in their cellular make-up to express Id-1 gene constitutively.

4. Constitutive Id-1 Expression Converts a Nonaggressive into a More Aggressive Breast Cancer Cell Line To test whether the unregulated Id-1 expression contributes to aggressive phenotype of human breast cancer cells and to determine if the induced constitutive Id-1 expression would convert nonaggressive cells into aggressive metastatic cells, constitutive Id-1 expression was investigated.

For this purpose, the human Id-1 cDNA was expressed in nonaggressive T47D cells using amphotropic retrovirus (pBabe-Id-1). Production of pBabe-Id-1 retroviral vector and virus are described in Example 1. Retroviral infection is described in Example 2. Puromycin was used to select virus-expressing cells.

Briefly, approximately eight RT-units of either pBabe-puro or pBabe-Id-1 retrovirus were mixed with 5 ml of medium containing 4 µg/ml polybrene and were added to T47D cells in 100-mm dishes. Cells expressing the retroviral genes were selected in 0.6 µg/ml puromycin, which killed all of the mock-infected cells within three days, whereas 80 or 30% of the pBabe-puro or pBabe-Id-1-infected cells, respectively, survived. The puromycin-resistant cells are referred to as T47D-pBO or T47D-Id-1. To establish single-cell clones, the T47D-Id-1 population was plated at 1-2 cells/well in 24-well tissue LXSN retroviral vector was prepared in the same way except neomycin was used to select virus expressing cells culture plates. Clones that grew in the wells were expanded. Results are seen in FIG. 3.

Figure 3:
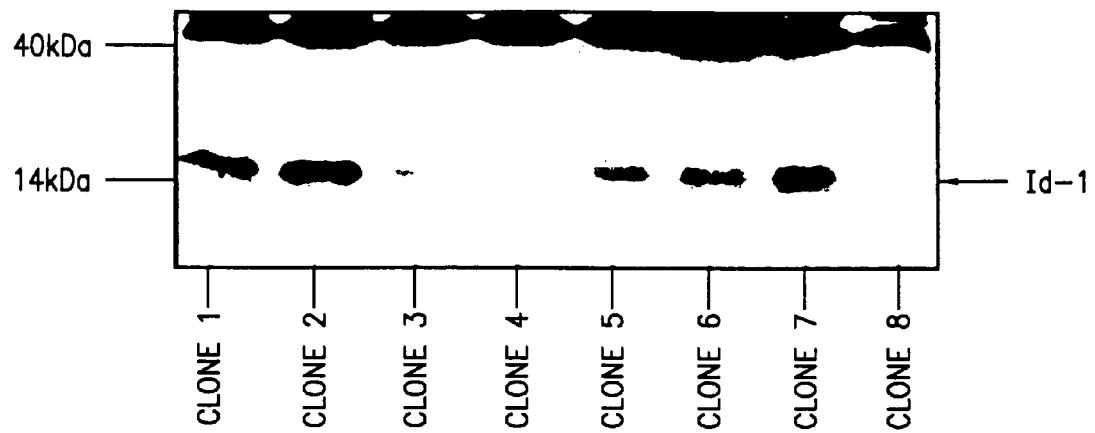
FIG. 3 is a Western analysis using a polyclonal antibody against human Id-1 protein with cross-reactive bands around $M_R$ 40,000 (40 Kda) indicating loading and transfer efficiency with nine cell clones of T47D-Id-1.

FIG. 3 illustrates Id-1 protein levels obtained in nine clones. When T47D cells were infected with pBabe-Id-1 retrovirus, nine single-cell-derived clones (clone 1-clone 9) were obtained. The clones were cultured in serum-free medium for two days before protein extraction and Western analysis using a polyclonal antibody against human Id-1. Positions of Id-1 protein and molecular weight markers in each clone are indicated. Cross-reactive bands around $M_r$ 40,000 (40kDa) indicate loading and transfer efficiency.

From nine single-cell-derived clones isolated from the T47D-Id-1 population, the clone 6 was lost during processing. Each of the eight surviving clones expressed a different level of Id-1 protein, as determined by Western analysis. Clones 1, 2, and 8 expressed relatively high levels of Id-1 protein in serum-free medium, whereas clones 4 and 9 expressed very low levels of Id-1 under these conditions. The other clones expressed Id-1 at intermediate levels.

Five T47D-Id-1 clones, expressing either high or low levels of Id-1 in serum-free medium, were then examined for invasiveness using the Boyden Chamber invasion assay. Conditions of the Boyden Chamber invasion assay are described in Example 5. Results are shown in FIG. 4.

Figure 4:
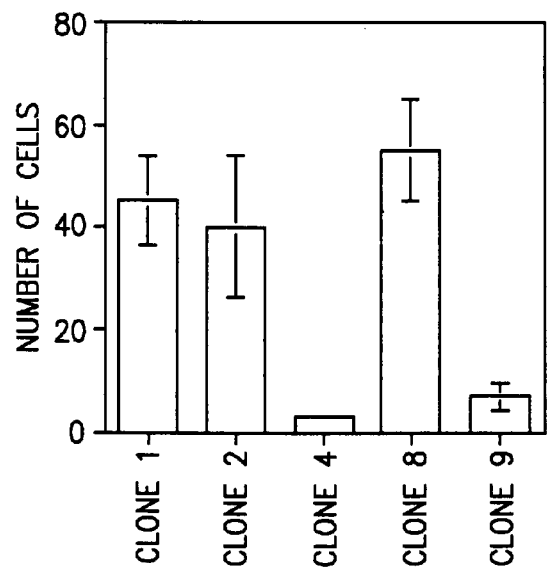
FIG. 4 is a graphical representation of Boyden Chamber invasion assay for T47D-Id-1 cell clones.

FIG. 4 illustrates Boyden Chamber invasion assay for T47D clones. Cells were cultured in serum-free medium for 2 days before they were placed in the upper chamber of Matrigel-coated trans-well filters. The invasion assay was carried out for 20 hours in serum-free medium and cells that migrated through the filter were stained and counted. Results were averaged and SDs were calculated.

As seen in FIG. 4, the invasive activity of each clone was approximately proportional to the level of Id-1 protein expression. Thus, clones with constitutively high levels of Id-1 (clones 1, 2, and 8) were more invasive then clones expressing low levels of Id-1 protein (clones 4 and 9). The invasive activity of the low-expressing clones resembled that of the uninfected parental T47D cells (not shown).

Ectopic Id-1 expression also conferred a growth advantage in serum-free medium, as measured by the percentage of cells incorporating [$^3$H]-thymidine. Conditions of the [$^3$H]-thymidine labeling are described in Example 6. Results are seen in FIG. 5.

Figure 5:
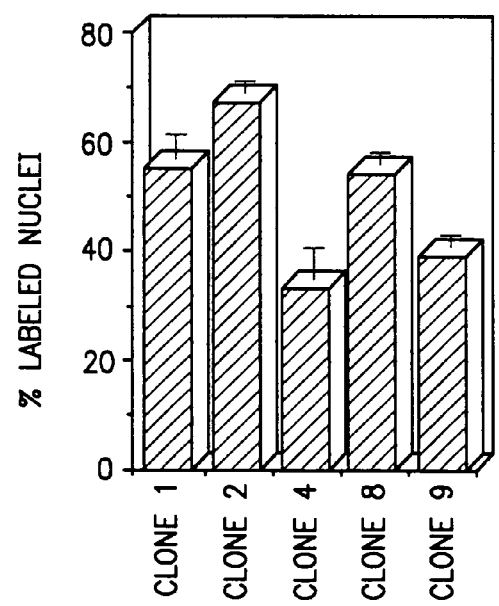
FIG. 5 is an autoradiogram of T47D cells incubated with [$^3$H]thymidine.

FIG. 5 shows percentage of labeled nuclei of cells cultured in serum-free medium for 32 hours before incubation with [$^3$H]-thymidine for additional 16 hours and processed by autoradiography. Cell that incorporated [$^3$H]-thymidine were calculated as a percentage of total DAPI-stained nuclei.

As seen in FIG. 5, the three T47D-Id-1 clones that expressed Id-1 proteins at higher levels had a greater [$^3$H]-thymidine-labeling index than two clones in which Id-1 expression was lower. The three T47D-Id-1 clones that expressed Id-1 protein at higher levels had a greater thymidine-labeling index than two clones in which expression of Id-1 protein was lower. Thymidine-labeling index for clones 1, 2 and 8 was 59%/average, for clones 4 and 9 it was 36%/average.

These results show that when normal Id-1 regulation is lost and Id-1 is constitutively expressed, human breast cancer cell lines acquire increased invasiveness and a proliferative advantage in a growth factor-deficient media. Ectopic Id-1 expression converted a relatively nonaggressive breast cancer cell line into a relatively aggressive one.

These results show that by determining a level of Id-1 protein expression, evaluation of the breast cells aggressivity can be made.

Since the above findings indicated that Id-1 expression may serve as a prognostic marker for certain subset of aggressive breast cancers, breast cancer biopsies for Id-1 expression were further examined by immunohistochemistry.

5. Id-1 Expression in Breast Cancer Biopsies

To determine whether the above obtained observations are applicable to humans, a large number of breast cancer biopsies were obtained from patients and immunohistochemical reactions as well as Western analyses were performed.

Immunohistochemical determination of the expression of Id-1 protein was carried out on a total of eighty-three breast cancer biopsies obtained from patients treated at California Pacific Medical Center.

Twenty-three of the biopsies were ductal carcinoma in situ (DCIS), sixty biopsies were infiltrating carcinomas of which twelve were Grade 1, seven were Grade 2 and forty-one were of Grade 3 carcinoma.

Out of twenty-three ductal carcinomas in situ (DCIS), 18 were found negative (78%), three were weakly positive (13%), and two were strongly positive (9%). Infiltrating carcinomas Grade 1, which is the least aggressive amongst the invasive tumors, displayed a pattern of Id-1 protein expression similar to the DCIS. Out of twelve Grade 1 carcinoma, 10 were negative (83%), 1 was weakly positive (8.5%), and 1 was strongly positive (8.5%). On the other hand, the majority of the infiltrating Grade 2 and Grade 3 carcinomas, the most aggressive tumors, were weakly or strongly Id-1 positive. Out of seven Grade 2 carcinomas, 3 were negative, 1 was weakly positive, and 3 were strongly positive. Out of forty-one Grade 3 carcinomas, 16 were negative (39%), 4 were weakly positive (10%), and 21 were strongly positive (51%).

Results are seen in Table 1.

TABLE 1

Id-1 Protein Expression Determined By Immunohistochemistry in 83 Breast Cancer Biopsies

| Tumor Type | Id-1 Negative | Id-1 Weakly Positive | Id-1 Strongly Positive |
|---|---|---|---|
| Ductal Carcinoma in Situ | 78% (18/23) | 13% (3/23) | 9% (2/23) |
| Infiltrating Carcinoma | | | |
| Grade 1 | 83% (10/12) | 8.5% (1/12) | 8.5% (1/12) |
| Grade 2 | 43% (3/7) | 14% (1/7) | 43% (3/7) |
| Grade 3 | 39% (16/41) | 10% (4/41) | 51% (21/41) |

Numbers in parenthesis indicate the actual number of biopsies out of the total number of biopsies examined.

Figure 6A:
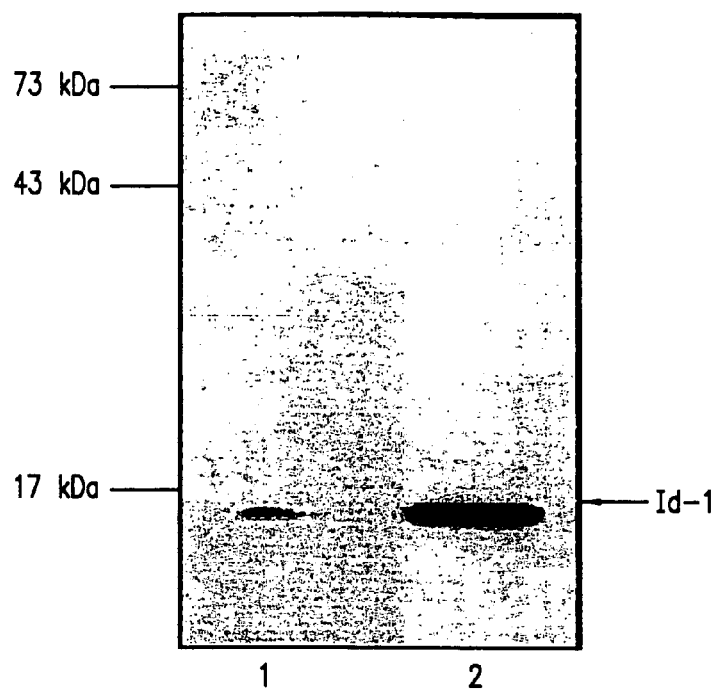
FIG. 6A is a Western analysis of an Id-1 protein expression probed with the Id-1 antibody in non-invasive cancer T47D (lane 1) and metastatic cancer MDA-MB-231 (lane 2) cells. The position of Id-1 protein is indicated.
Figure 6B:
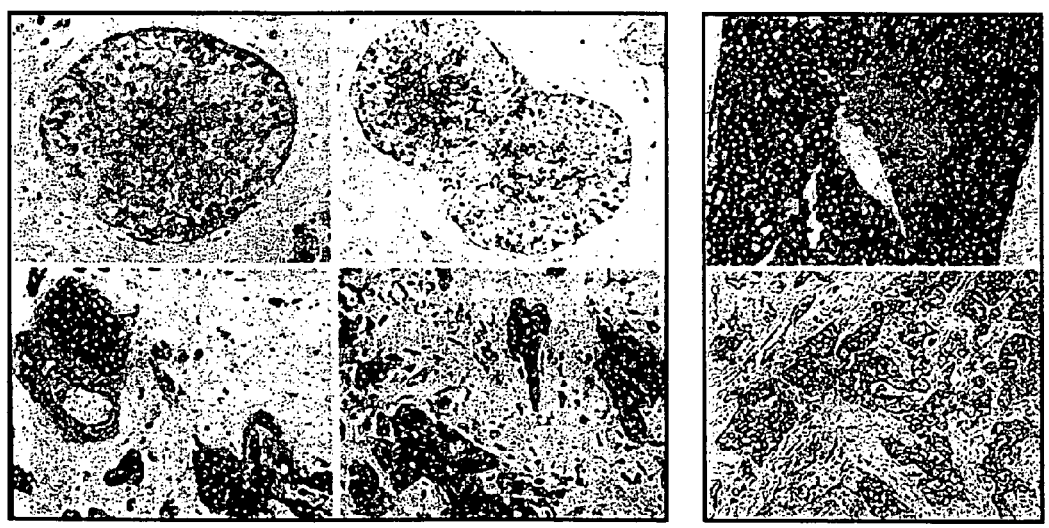
FIG. 6B is an immunohistogram wherein panels (a), (b), and (c) are representative sections from ductal carcinomas in situ (DCIS), and panels (d), (e), and (f) are Grade 3 invasive carcinomas analyzed by immunohistochemistry with anti Id-1 anti-serum.

Results of six selected representative samples in this assay are seen in FIGS. 6A and 6B which show expression of Id-1 in human breast cancer biopsies. Immunohistochemistry was carried out using a specific batch of anti-Id-1 antibody, confirmed by Western analysis to show no cross-reactive bands. Immunohistochemical procedure is described in Example 8.

FIG. 6A is a Western analysis showing the specificity of the Id-1 antibody used for immunohistochemistry. Lane 1 shows non-invasive T47D cancer cells, lane 2 shows invasive and metastatic MDA-MB-231 cancer cells. All cells were cultured in serum-free medium for 48 hours. Position of Id-1 protein is indicated. No cross-reactive band is seen. Results shown in FIG. 6A clearly confirm high expression of Id-1 protein in the cancer cells when compared to Id-1 expression in T47D cells.

FIG. 6B shows representative section from DCIS (panels a, b, and c) and Grade 3 invasive carcinoma (panels d, e and f) which were analyzed by immunohistochemistry using antiserum against Id-1 protein. The majority of DCIS were negative (panels a and b), one showed strong positivity in its large ductal structure (panel c) . The majority of infiltrating carcinoma, on the other hand, showed strong Id-1 immunoreactivity (panel d and e) . Minority of the invasive tumors were negative (panel f). In panel d, a differentiated glandular section, the structure with the lumen was negative whereas infiltrating cells showed strong immunoreactivity.

These results show that almost all examined ductal carcinomas in situ (DCIS) were negative for Id-1 staining. However, the majority (51%) of infiltrating Grade 3 carcinomas of ductal origin were strongly Id-1 positive. These results confirm that Id-1 is a reliable prognostic marker for breast cancer invasiveness and metastatic propensity.

6. Expression of Id-2 in Human Breast Cancer Cells

To determine if the expression of Id-1 protein was specific to aggressive malignant cancer cells or if this was common property of Id proteins, the expression of the second Id protein, namely Id-2 protein, in human breast cancer cells was examined.

Id-2 expression in human cancer cells was determined by Northern analysis. The same four types of cells were used as used previously in studies with Id-1. These cells were cultured in serum-free medium for two days before RNA was extracted. The blot was hybridized with a human Id-2 cDNA probe. Results are shown in FIG. 7.

Figure 7:
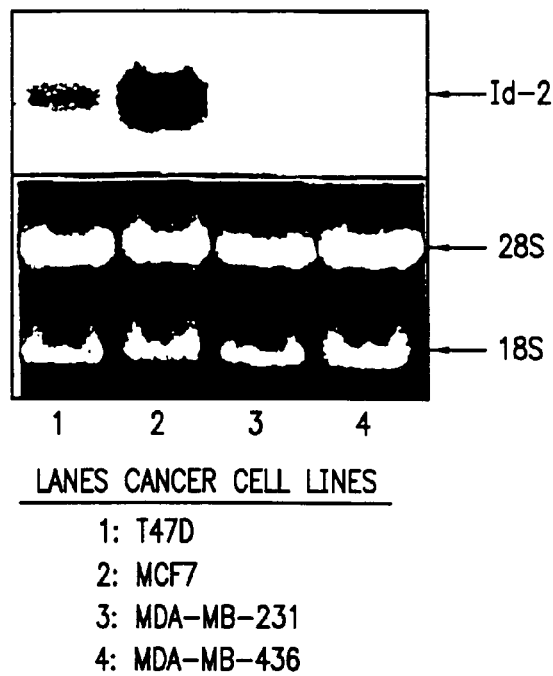
FIG. 7 is a Northern blot showing Id-2 mRNA expression in human breast cancer cell lines cultured in serum-free medium for two days.

FIG. 7 is a Northern analysis of Id-2 transcripts. Upper panel shows expression of Id-2 mRNA in non-invasive T47D (lane 1) and MCF7 (lane 2) cancer cells and in highly aggressive, metastatic and invasive MDA-MB-231 (lane 3) and MDA-MB436 (lane 4) cancer cells. Lower two panels show a positions of two ribosomal 28S and 18S RNA used as control for RNA integrity.

FIG. 7 shows that under the same experimental conditions as those described for Id-1, Id-2 mRNA was found to be expressed in lanes 1 and 2, which correlate with non-invasive T47D and the MCF7 human breast cancer cell lines. As seen in FIG. 7, lanes 3 and 4, there was no detectable Id-2 mRNA in lanes 3 or 4, which represent highly invasive MDA-MB-231 and MDA-MB-436 human breast cancer cell lines.

Thus, in contrast to Id-1, the expression of Id-2 gene products, such as the protein and mRNA, correlates with non-aggressive or non-invasive cancers.

These results show that both Id-1 and Id-2 are fair indicators of breast cancer presence and aggressivity and that each indicates and is found in a different type of cancer cells. Detection of Id-1 expression indicates presence of highly aggressive, metastatic and invasive cancer cells. Detection of Id-2 expression indicates presence of noninvasive cancer cells.

7. Inverse Correlation Between Id-1 and Id-2 Expression

A direct regulatory link has been found to exist between Id-1 and Id-2 genes in breast cells. Id-2 protein expression is generally high when Id-1 protein expression is low, both in vitro and in vivo, confirming an existence of a negative correlation in expression levels.

a. Id-2 Expression In Vitro

To determine the pattern of Id-2 expression during mammary cell growth and differentiation, expression of Id-2 protein during mammary epithelial cell differentiation in vitro and in vivo was undertaken.

For this purpose, the yeast two-hybrid system and the basic helix-loop-helix protein ITF-2 as a bait were used to isolate Id-2 from a library derived from differentiated, milk-producing mammary epithelial cells. First, Id-2 protein expression in SCp2 cells during proliferation or differentiation was investigated, using Western analysis. Results are shown in FIG. 8.

Figure 8:
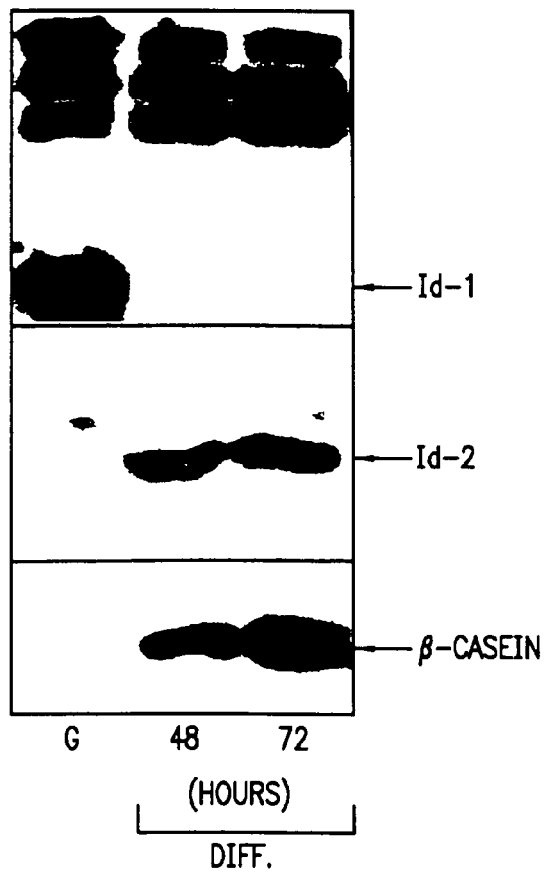
FIG. 8 is a Western analysis showing inverse correlation between Id-1 and Id-2 protein expression in growing (G) and differentiated (Diff) mouse mammary SCp2 epithelial cells in culture.

FIG. 8 is a Western analysis showing inverse correlation between Id-1 and Id-2 protein expression in growing (G) and differentiated (Diff) SCp2 mammary epithelial cells treated with Matrigel and lactogenic hormones for 48 and 72 hours. Protein was extracted and analyzed using antibodies specific for Id-1, Id-2 and β-casein milk protein, which is the marker for mammary epithelial cells differentiation.

As shown in FIG. 8, differentiated cells expressed high levels of the Id-2 (16 kDa) protein, similarly to expression of β-casein, at both 48 and 72 hours. In comparison, Id-1 protein was detectable only in proliferating cells (lane G). No expression of Id-1 protein was detected in differentiated cells. These results clearly show that there is an inverse correlation between Id-1 and Id-2 protein.

To confirm this inverse correlation between Id-1 and Id-2 expression, Northern analysis of SCp2 cells proliferating or treated with laminin for 24 and 48 hrs was performed. Laminin is an important component of extracellular matrix and can trigger differentiation. Results are seen in FIG. 9.

Figure 9:
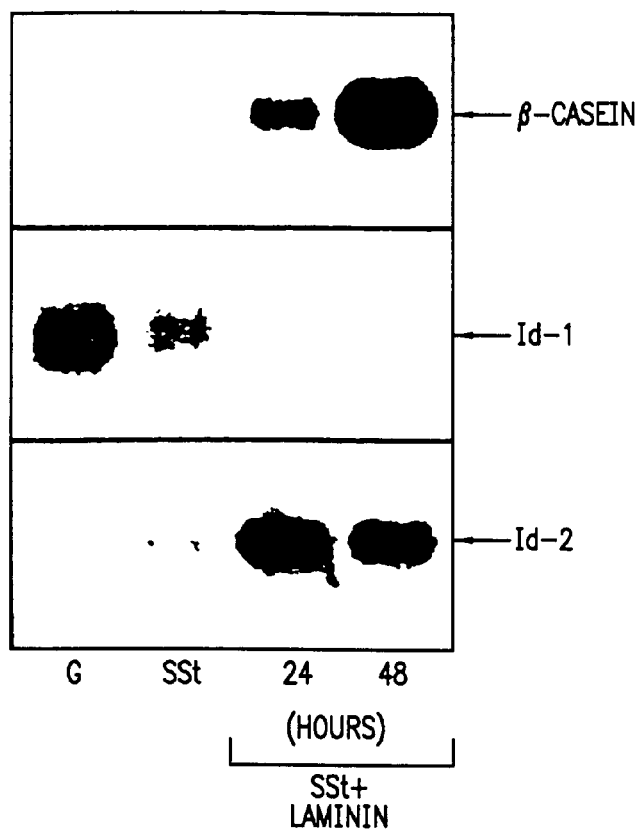
FIG. 9 is a Northern mRNA analysis showing an inverse correlation between Id-1 and Id-2 mRNA expression in growing (G), serum starved (SSt) and laminin-treated mouse mammary SCp2 cells in culture for 24 and 48 hours.

FIG. 9 is a Northern analysis of inverse correlation between Id-1 and Id-2 mRNA expression in growing (G), serum starved (SSt), and Laminin-treated SCp2 mammary epithelial cells for 24 and 48 hours. Total RNA was extracted and analyzed using probes specific for Id-1, Id-2 and β-casein.

Results seen in FIG. 9 confirm results seen in FIG. 8. There was expression of both Id-2 and β-casein in differentiated cells, but there was no expression of Id-1 in these cells. Id-1 was expressed only in growing (G) cells confirming that the inverse correlation exists between expression of Id-1 and Id-2 mRNA.

In order to determine if Id-2 up-regulation was a crucial event for mammary epithelial cell differentiation and milk production, two sets of experiments were performed. In the first set, SCp2 cells were treated with Laminin and lactogenic hormones for 48 hrs in the presence of either control oligonucleotides or Id-2 antisense oligonucleotides. Results are seen in FIG. 10.

Figure 10A:
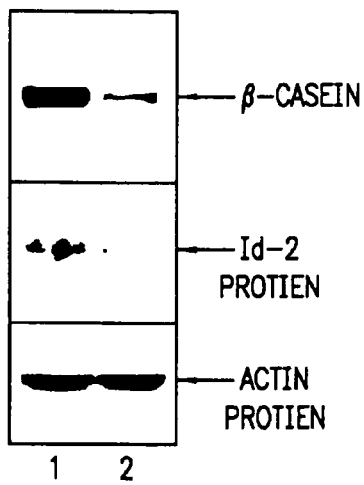
FIG. 10A shows reduction of β-casein expression in mammary epithelial cells treated with Id-2 antisense oligonucleotides.
Figure 10B:
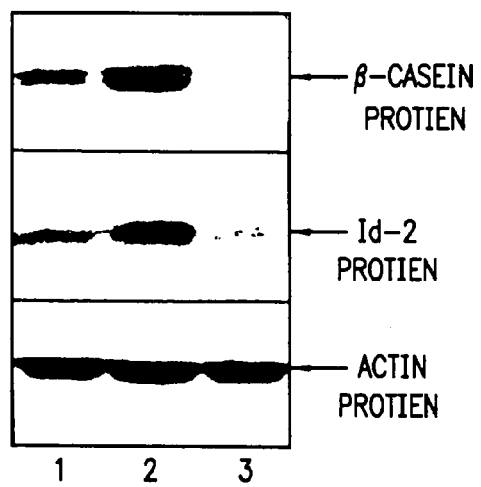
FIG. 10B shows increase of β-casein expression in mammary epithelial cells infected with a LXSN-Id-2-sense and Id-2-antisense expression vectors.

FIG. 10A illustrates reduction of β-casein expression in mammary epithelial cells treated with Id-2 antisense oligonucleotides. Lane 1 shows SCp2 cells treated with Laminin for 48 hours and control oligonucleotide. Lane 2 shows Scp2 cells treated with Laminin for 48 hours and with Id-2 oligonucleotide. FIG. 10B illustrates increase of β-casein expression in mammary epithelial cells infected with a LXSN-Id-2 sense expression vector (Lane 2) and inhibition of β-casein expression in cells infected with a LXSN-Id-2 antisense expression vector (Lane3) . Lane 1 corresponds to cells infected with a LXSN-control vector.

As seen in FIG. 10A, a dramatic reduction of β-casein expression was observed in Id-2 antisense oligonucleotide treated cells. In the second set of experiments, SCp2 cells were infected with either LXSN-control, LXSN-Id2-sense or LXSN-Id2-antisense constructs, selected with neomycin and treated with laminin for 48 hrs. As shown in FIG. 10B, β-casein expression was increased in SCp2-LXSN-Id2-sense cells in comparison to control. Most dramatically, β-casein expression was almost undetectable in SCp2-LXSN-Id2-antisense cells.

The results seen in FIGS. 10A and 10B show that Id-2 is involved and necessary in and its up-regulation occurs during mammary cell differentiation. However, the results in FIG. 10B also shows that such up-regulating can be effectively negated with Id-2 antisense carrying construct.

b. Id-2 Expression In Vivo

To determine Id-2 protein expression in vivo and to compare it to the expression of Id-1 protein, another set of experiments was performed.

In these studies, the level of Id-1 and Id-2 mRNA during mammary gland development in vivo, using Northern analyses of total RNA from virgins, pregnant and lactating mice were determined. Results are seen in FIG. 11.

Figure 11:
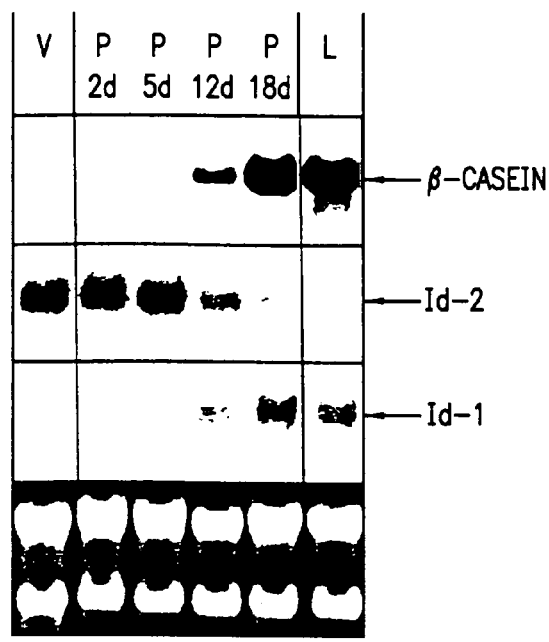
FIG. 11 is a Northern mRNA analysis displaying a different pattern of expression in the mouse mammary gland in vivo at different stages of development wherein V indicates virgin, P indicates pregnant and L indicates lactation stage. Northern analysis was performed using cDNA probes for mouse β-casein, Id-1 and Id-2.

FIG. 11 shows a different pattern of Id-1 and Id-2 protein expression in the mouse mammary gland in vivo. Total RNA was extracted from mouse mammary glands at different stages of development. Northern analyses using cDNA probes for mouse β-casein, Id-1 and Id-2 were performed. V indicates virgin; P indicates pregnant at days 2, 5, 12 and 18 and L indicates lactation mammary gland.

As seen in FIG. 11, β-casein mRNA was evident only during mid and late pregnancy and during lactation. When the blot was then reprobed with a mouse Id-1 cDNA, Id-1 mRNA expression resulted. Such Id-1 expression was inversely correlated with β-casein expression, suggesting a similar role for Id-1 gene in vivo to that observed in the SCp2 cells, that is, Id-1 expression declines when the mammary gland proceeds towards full differentiation as, for example, in lactation stage. On the other hand, expression of Id-2 mRNA was barely detectable in virgin gland and at the beginning of pregnancy. Its expression increased at day 12 of pregnancy, when epithelial cells start producing the milk protein β-casein. Id-2 expression was at its highest level toward the end of pregnancy (day 18) and lactation, when the epithelial cells were fully differentiated.

The above results show that the expression pattern of Id-2 mRNA or gene expression is different from that of Id-1 MRNA. Id-2 expression level is opposite to that of Id-1 expression during periods of cell growth and differentiation. This further indicates a differentiating role for Id-2, in contrast to Id-1, during mammary gland development.

The terminal development of the mammary gland involves the contribution of proliferative as well as differentiative events. These events must be tightly coordinated. Id-2 as well as Id-1 were shown to play a central role in this regulation by negatively regulating different sets of bHLH proteins. Moreover, the expression of these two genes was found to be tightly coordinated.

c. Analysis of Id-2 Expression in Breast Cancer Cells

To confirm that similar findings to those found in murine mammary epithelial cells in vitro and in vivo, Id-2 expression was investigated in human breast cancer cell lines in culture using the same mouse Id-2 cDNA probe.

For this purpose, the two T47D and MCF7 cancer cell lines which display non-aggressive and differentiated characteristics in culture (in absence of estrogen), and the two highly aggressive and metastatic MDA-MB-231 and MDA-MB-436 cell lines were used. The cells lines were described above. Results are seen in FIG. 12.

Figure 12A:
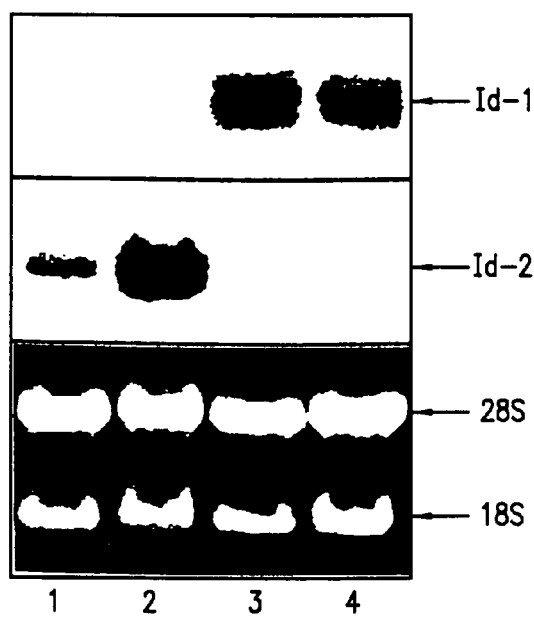
FIG. 12A is a Northern analysis of Id-1 and Id-2 mRNA expression in human breast cancer cell lines. Cell were cultured in serum-free medium for 48 hours before RNA was extracted. Lane 1: T47D; lane 2: MCF-7; lane 3: MDA-MB-231 and lane 4: MDA-MB-436 cell lines.
Figure 12B:
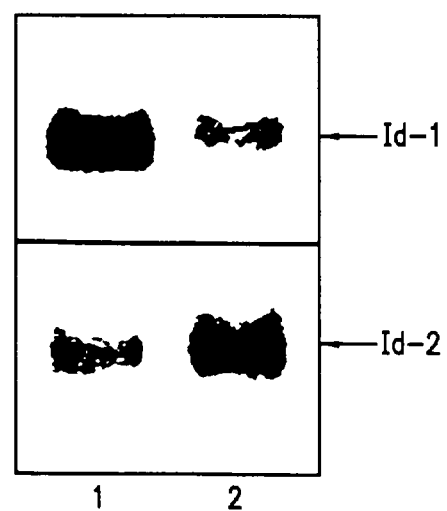
FIG. 12B shows Id-1 and Id-2 expression in MCF-7 growing in 10% FBS (lane 1) and MCF-7 cultured in serum-free medium for 24 hours (lane 2).

FIG. 12A is a Northern analysis of Id-1 and Id-2 mRNA expression in human breast cancer cell lines. Cells were cultured in serum-free medium for 48 hours before RNA was extracted and subjected to blotting. Lane 1 shows T47D cancer cell line; lane 2 shown MCF-7 cancer cell line; lane 3 shows MDA-MB-231 cancer cell line and lane 4 shows MDA-MB-436 cancer cell line. FIG. 12B shows Id-1 and Id-2 expression in MCF-7 growing in 10% FBS (lane 1) and MCF-7 cultured in serum-free medium for 24 hours (lane 2).

As seen if FIG. 12A, when cultured in serum-free conditions for 48 hrs, MCF-7 cells, and to a lesser extent T47D cells, expressed high levels of Id-2 mRNA. However, Id-2 expression was undetectable in the two aggressive cell lines MDA-MB-231 and MDA-MB-436 where, as expected, Id-1 was highly expressed. Id-1 expression was not detected in non-aggressive T47D and MCF-7 cancer cells.

These results again confirm, this time in human breast cancer cells, the inverse correlation between the expression of the two HLH proteins that was previously determined to exist in mammary epithelial cells and imply a different role for Id-2 from Id-1 in breast cancer cell phenotypes. This is seen especially clearly in FIG. 12B, where, upon serum-withdrawal, the levels of Id-2 mRNA were found to be increased in MCF-7 cells whereas the levels of Id-1 MRNA were decreased.

All the data presented above clearly show the role of the two helix-loop-helix proteins, Id-1 and Id-2, as molecular switches not only between growth/invasion and differentiation in mammary epithelial cells, but also during breast cancer progression.

8. Targeting Id-1 Reduces Breast Cancer Cell Invasion In Vitro

To determine whether the Id-1 is a key gene which regulates the aggressive phenotype of human breast cancer cells, studies were performed to determine whether Id-1 antisense expression converts a very aggressive and metastatic breast cancer cell into a non-aggressive one.

For this purpose, the human Id-1 cDNA was expressed in a sense as well as an antisense orientation in human metastatic MDA-MB436 breast cancer cells using an amphotropic LXSN-Id-1 sense and antisense retrovirus. Neomycin was used to select for virus-expressing cells. Results are shown in FIG. 13.

Figure 13:
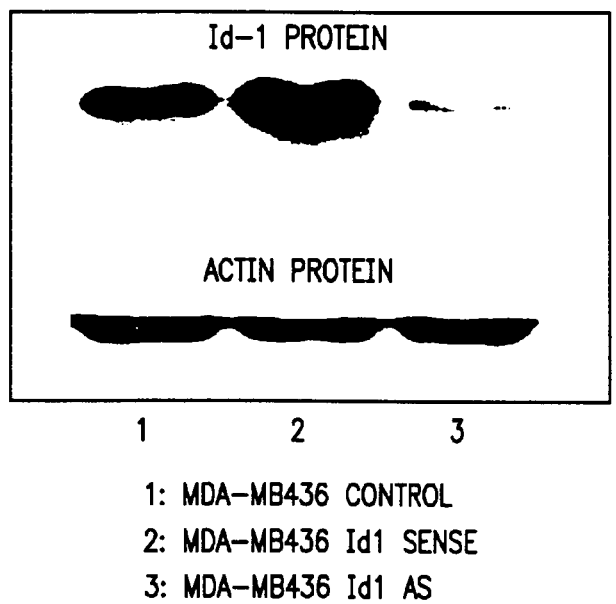
FIG. 13 is a Western blot showing Id-1 protein expression. Lane 1 shows MDA-MB436 controls, lane 2 shows MDA-MB436 Id-1 sense infected with an amphotropic retrovirus and lane 3 shows MDA-MB436 Id-1 antisense infected with an amphotropic retrovirus.

FIG. 13 is a Western analysis of Id-1 expression of highly aggressive and invasive MDA-MB436 cancer cells. Actin was used as control. Lane 1 shows MDA-MB436 cells as control against MDA-MB436 treated with Id-1 sense retrovirus (lane 2) or MDA-MB436 treated with Id-1 antisense infected with retrovirus (lane 3).

As seen in FIG. 13, cells infected with a control virus (empty plasmid, lane 1) expressed detectable levels of Id-1 protein in serum-free medium. The LXSN-ld-1 sense infected population (lane 2) expressed even higher levels of Id-1 protein whereas the LXSN-Id-1 antisense infected cells (lane 3) expressed very low levels of Id-1 under these conditions.

The same three populations of cells were then tested in a Boyden Chamber invasion assay to compare their ability to migrate and invade a reconstituted basement membrane. Results are seen in FIG. 14.

Figure 14:
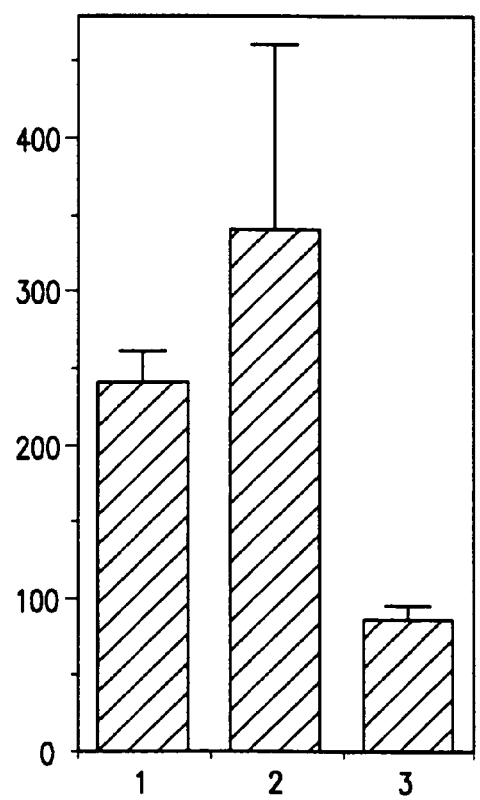
FIG. 14 is graphical illustration of FIG. 13 showing a conversion of aggressive MDA436 cells into non-aggressive cells when treated with Id-1 antisense amphotropic retrovirus in an in vitro invasion assay.

FIG. 14 shows results of the invasion assay where the assays were performed in modified Boyden Chambers assay described in Example 5 with 8 μm pore filter inserts for 24-well plates obtained from Collaborative Research. Filters were coated with 10-12 μl of ice-cold Matrigel (7.3 mg/ml protein) obtained from Collaborative Research. Cells (100, 000 per well) were added to the upper chamber in 200 μl of the appropriate medium containing 0.1% bovine serum albumin (BSA). In general, cells were assayed in triplicate or quadruplicate, and the results averaged. The lower chamber was filled with 300 μl of NIH-3T3 cell-conditioned medium according to Cancer Res., 47:3239-3245 (1987). After a 20 hours incubation, cells were fixed with 2.5% glutaraldehyde in PBS and stained with 0.5% toluidine blue in 2% $Na_2CO_3$. Cells that remained in the Matrigel or attached to the upper side of the filter were removed with cotton tips. Cells on the lower side of the filter were counted using light microscopy.

The invasive activity of each cell population was proportional to the level of Id-1 protein expression as seen in Western blot shown in FIG. 13. The population with high levels of Id-1 (LXSN-Id-1 sense cells, lane 2) was much more invasive than the population expressing low levels of Id-1 (LXSN-Id-I antisense cells, lane 3). The invasive activity of the control population expressing intermediate levels of Id-1 protein was also intermediate (lane 1).

These results further confirm that the aggressivity and invasiveness of the human breast cancer cells can be attributed to the high expression of Id-1 gene and also show that aggressivity of cells expressing Id-1 protein can be reduced or eliminated by treatment with an Id-1 antisense constructs. Consequently, the expression of Id-1 in human breast cancer cells is a good prognostic and diagnostic tool for detection of aggressive breast cancer and for distinguishing such aggressive and invasive cancer from the non-invasive cancer cells attributable to their expressing Id-2 protein.

9. Targeting Id-1 Reduces Breast Cancer Cell Metastasis In Vivo

Following the finding that targeting Id-1 with an antisense comprising construct reduces aggressivity of breast cancer cells in vitro, further studies were undertaken to determine if the same would be valid for breast cancer cells in vivo, and if the metastatic propensity of cancer cells expressing Id-1 could be changed to nonaggressive cells.

In order to determine the role of Id-1 in the metastatic process in vivo, the 4T1 murine metastatic breast cancer cell line which express, like human MDA-MB231 and MDA-MB436 cells, high levels of Id-1 mRNA and protein and which metastasize to the lungs were used. In order to deliver the Id-1 antisense constructs, the technique of cationic liposome-DNA complex (CLDC)-based intravenous gene delivery according to *J. Biol. Chem.*, 274:13338-13344(1999) was utilized. This CLDC-based intravenous (iv) delivery (tail vein injections) of Id-1 antisense construct, such as plasmid, significantly reduced the metastatic spread of 4T1 breast cancer cells in 4T1BalbC mice. Results are seen in FIG. 15.

Figure 15:
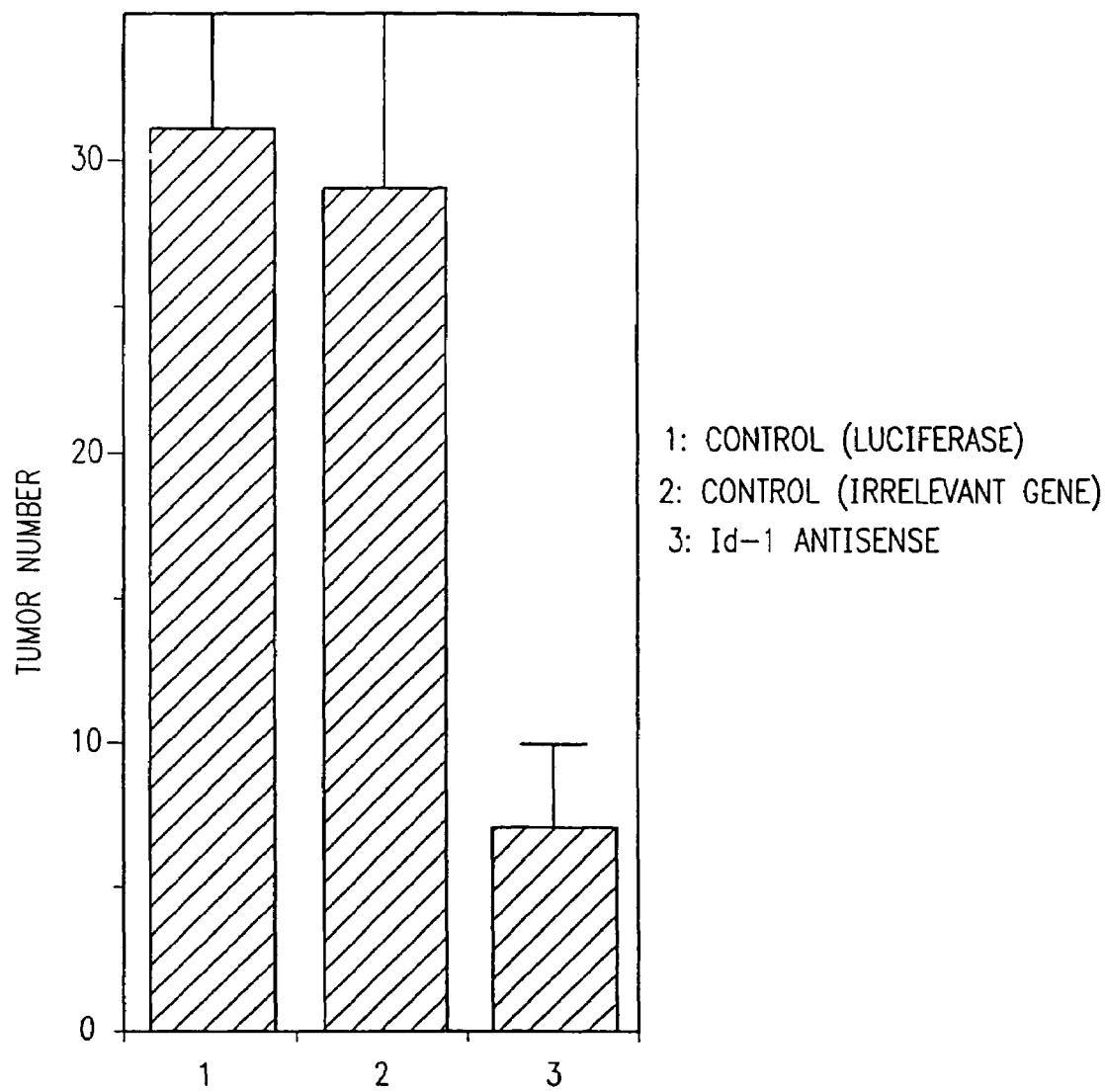
FIG. 15 is a graph showing decrease in tumor number in 4T1/BalbC mice treated with various constructs in vivo.

FIG. 15 is a graph illustrating a tumor reduction in 4T1/BalbC mice treated with various constructs. Specifically, the mice were treated with luciferase (lane 1), with irrelevant gene serving as another control (lane 2) and with Id-1 antisense (lane 3).

Results shown in FIG. 15 clearly show that the number of highly aggressive and metastatic tumor decreases significantly when the tumor cells are targeted with Id-1 antisense construct.

Specifically, a single injection of CLDC containing Id-1 antisense, three days after iv injection of 50,000 4T1 cells, dramatically reduced the total number of lung metastases (lane 3), when compared to tumor-bearing mice treated with CLDC containing control genes (luciferase as well as an irrelevant gene, lanes 1 and 2).

These results show first that the aggressive tumor growth and metastasis can be treated with antisense Id-1 construct and, second, that CLDC-based plasmid antisense delivery, which is a novel delivery approach, is a practical way of achieving such delivery.

10. Cumulative Evidence for Id-1 and Id-2 Function in Breast Cancer Aggressivity and Diagnosis and Treatment Thereof Invention described herein showed that aggressive metastatic breast cancer cells express high levels of Id-1 mRNA because of a loss of serum-dependent relation that is mediated by the 2.2-kb region of the human Id-1 promoter. This suggests that unregulated Id-1 gene expression may be an important regulator of the aggressive phenotype of a subset of human breast cancer cells. The results disclosed herein further implicated Id-1 gene as a critical downstream target of steroid hormones and critical mediator of the aggressive phenotype in a subset of human breast cancer cells.

Specific findings are as follows:

The Id-1 gene is highly expressed during proliferation, and is down-regulated when mammary epithelial cells differentiate. The Id-2 gene is not expressed in growing mammary epithelial cells, and is up-regulated during differentiation.

Id-1 expression declines when the mammary gland proceeds toward full differentiation during pregnancy and at the lactation stage. Id-1 thus is expressed primarily in cells which are nondifferentiated or begin to differentiate.

In non-invasive breast cancer cell, the expression of Id-1 gene can be induced by culturing these cells in the presence of serum. However, in these non-invasive breast cancer cells, this gene is not expressed and the expression cannot be induced in serum-free medium. To the contrary, the invasive metastatic cancer cells express Id-1 gene in both the serum containing and serum-free medium. Consequently, the invasive metastatic breast cancer cells do not need Id-1 expression induction by serum but it is in their cellular make-up to express Id-1 gene constitutively.

The constitutive expression of Id-1 inhibits differentiation of mammary epithelial cells, and induces proliferation and invasion.

Certain aggressive breast cancer cells constitutively express high levels of Id-1 protein, apparently due to the loss of serum-dependent regulation.

The expression of Id-1 directly correlates with the level of aggressiveness in breast cancer cell lines and evaluation of the breast cells aggressivity can be made in breast cancer biopsies by determining a level of Id-1 protein expression. Almost all examined ductal carcinomas in situ (DCIS) were negative for Id-1 staining. However, the majority (51%) of infiltrating Grade 3 carcinomas of ductal origin were strongly Id-1 positive. These results confirm that Id-1 is a reliable prognostic marker for breast cancer invasiveness and metastatic propensity.

The expression of Id-2 directly correlates with the level of differentiation and non-aggressiveness breast cancer cells. Id-2 is involved in and its up-regulation occurs during mammary cell differentiation. Such up-regulating can be effectively negated with Id-2 antisense carrying construct.

Id-1 and Id-2 are fair indicators of breast cancer presence and aggressivity and each indicates and is found in a different type of cancer cells. Detection of Id-1 expression indicates presence of highly aggressive, metastatic and invasive cancer cells. Detection of Id-2 expression indicates presence of non-invasive cancer cells. The expression pattern of Id-2 protein is different from that of Id-1 protein. Id-2 expression level is opposite to that of Id-1 expression during periods of cell growth and differentiation.

The expression of Id-1 in human breast cancer cells is a good prognostic and diagnostic tool for detection of aggressive breast cancer and for distinguishing such aggressive and invasive cancer from the non-invasive cancer cells attributable to their expressing Id-2 protein.

The aggressive tumor growth can be treated with antisense Id-1 construct and CLDC-based plasmid antisense delivery is a practical way of achieving such delivery.

The Id-2 protein level changes dramatically at different stages of breast development in the opposite direction of the Id-1 protein level. The increase in the level of Id-2 protein is crucial for normal breast development, and breast cancer cells that produce high levels of Id-2 protein do not, or are less likely to, migrate and invade. They will remain localized in the breast, will not metastasize and are therefore easier to treat.

II. Method for Detection, Diagnosis and Prognosis of Breast Cancer

A method for detection of the aggressive and invasive cancer cells or noninvasive cancer cells comprises detection of Id-1 and/or Id-2 genes, or their ratio, or Id-1 and/or Id-2 products, or their ratio, as diagnostic markers for detection of metastatic aggressivity of carcinoma. Such detection is useful both for diagnostic and particularly for prognostic purposes in patients.

As earlier noted, Id-I protein is expressed at elevated levels in aggressive breast cancer cell lines. These highly aggressive breast cancer cells have lost serum-dependent regulation of the Id-1 gene expression, which results in constitutively high levels of Id-1 protein. Indeed, it appears that the Id-1 protein plays a key role in the malignant progression of a subset of aggressive and invasive human breast cancers.

While Id-1 represents a marker of poor prognosis for invasive and metastatic breast cancer, in contrast Id-2 represents a marker of good prognosis for breast cancer since the breast cancer cells expressing Id-2 will tend to be localized and not metastasized.

A patient found to have breast cancer, but breast cancer in which Id-2 is being expressed, is one for whom the prospect of recovery by simpler and less invasive techniques, such as lumpectomy, is suggested. Such a patient, therefore, likely does not need the more radical treatments, such as mastectomy, radiation or chemotherapy, that would otherwise be recommended for invasive breast cancer when the high expression of Id-1 protein is detected.

A. Methods Suitable For Detection of Id-1/Id-2 Expression Products

In a therapeutic method of this invention described below, the treating physician who has, for example, found tumors/lumps will typically send a breast tissue sample, as a biopsy, to a pathologist for examination and diagnosis.

The examination and classification of the tissue is typically based on a visual inspection of tissue morphology. For example, the pathologist can decide whether the biopsied tissue is an infiltrating or invasive carcinoma or whether it is ductal carcinoma in situ (DCIS). Within each of these classifications the pathologist attempts to assign grades of aggressiveness, such as infiltrating Grade 1 carcinoma, which is not overly aggressive, or infiltrating Grade 3 carcinoma that is very aggressive.

The development of a DCIS into a highly aggressive and metastatic breast tumor involves a series of sequential steps; breast epithelial cells must lose the ability to interact with other cells, acquire the ability to digest the surrounding basement membrane, migrate toward the blood stream, and survive and proliferate in ectopic sites. Invasiveness marks the onset of metastasis, which is a hallmark of often final malignant progression.

For detection of Id-1/Id-2 proteins, the immunohistochemistry analysis using Id-1 antibodies can be used together with Id-2 antibodies, since a determination of both Id-2 and Id-1 expression, or lack of expression for one with respect to the other, will help the treating physician and pathologist determine the type or grade of breast cancer. Thus, determination of Id-1 or Id-2 expression ratio, or the ratio of Id-1 to Id-2 gene product such as proteins or mRNA, can be performed by various detection methods known to the art such as immunohistochemistry or in situ hybridization.

Where the gene products to be determined are proteins, then the Id-1 and Id-2 proteins can be detected and analyzed, for example, by immunohistochemistry as described in Examples 8 and 10, where anti-serum is directed against the gene product of interest.

Additionally, the presence or absence of a gene product, mRNA, can be detected in accordance with this invention through the use of probes, primers or anti-sense molecules. Such detection utilizes, for example, probes for detecting and/or analyzing Id-1 and Id-2 expression, such as in situ hybridization to detect target mRNA.

Where the Id-1 and Id-2 gene products to be detected are, for example, mRNA, then the detection can be accomplished, for example, with nucleic acid probes. Other means for detecting the presence or absence of the mRNA gene product that are known and useful can utilize primers and anti-sense molecules.

The DNA of the invention encoding the Id-1 or Id-2 gene or homologues, analogues, or fragments thereof may be used in accordance with the invention to diagnose disease states which are phenotypic of an aberrant Id-1 or Id-2 genotype or of aberrant Id-1 or Id-2 expression.

By way of another example, but not by way of limitation, many tumors may be characterized by a lack of, or excess of, Id-1 or Id-2 activity which may stem from mutations in the Id-1 or Id-2 coding or regulatory sequence.

In both of the examples above, afflicted cells, tissue sections or biopsy specimens may be screened with the Id-1 or Id-2 DNA sequences of the invention and isolated Id-1 or Id-2 sequenced to determine which mutations in Id-1 or Id-2 are associated with the diseases. The DNAs of the invention may also be used to determine whether an individual carries an aberrant Id-1 or Id-2 gene.

The detection of the aberrant Id-1 or Id-2 DNA is conducted by PCR amplification, from a small tissue sample. Detection of Id-1 or Id-2 product may also be via in situ hybridization or immunocytochemistry of pathology or biopsy specimens.

The best mode contemplated for practicing the invention for detection of breast cancer cell aggressivity is to perform assays from biopsied breast tissue for both Id-1 and Id-2 proteins or mRNAs. In practice, one or more of the sections made from an embedded biopsy are tested for Id-1 and for Id-2. The results are then compared for ratios of Id-1 and Id-2, since it appears that Id-1 and Id-2 are inversely correlated. The importance of determining the ratios of Id-1 and Id-2 will be specific for breast tissue and breast cancers, by contrast to other tissues and other cancers, where different ratios may be found.

B. Antibodies

In addition, Id-I and Id-2 antibodies can be used in a number of other detection methods, since many of the detection methods known in the art that will be useful in detecting Id-1 and Id-2 gene products utilize antibodies.

One aspect of this invention is a method for using Id-1 and Id-2 antibodies where the antibodies will bind to Id-1 and Id-2 proteins, respectively, if present, in a breast, cervical, ovarian, endometrium, squamous cells, prostate or melanoma tissue sample. The presence of bound antibodies can be determined by simple visual examination, or can be detected by other known methods, such as radioactivity or fluorescence.

For the production of antibodies, various host animals may be immunized by injection with the Id-2 or Id-1 gene product, or a portion thereof including but not limited to, portions of the Id-1 or Id-2 gene product in a recombinant protein. Such host animals may include but are not limited to rabbits, mice, and rats, to name but a few.

Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Id-1 and Id-2 antibodies are commercially available. The commercially available antibodies are typically polyclonal, and bind to both the mouse and human proteins.

Monoclonal antibodies may be prepared by using any technique which provides for the production of antibody molecules by continuous cell lines in culture. These include but are not limited to the hybridoma technique originally described in *Nature*, 256:495-497 (1975), the human B-cell hybridoma technique, *Immunology Today*, 4:72 (1983), *Proc. Natl. Acad. Sci.*, 80:2026-2030 (1983) and the EBV-hybridoma technique, *Monoclonal Antibodies and Cancer Therapy*, Alan R. Liss, Inc., pp. 77-96 (1985).

In addition, techniques developed for the production of "chimeric antibodies", *Proc. Natl. Acad. Sci.*, 81:6851-6855 (1984), *Nature*, 312:604-608 (1984), *Nature*, 314:452-454 (1985) by splicing the genes from a mouse antibody molecule of appropriate antigen specificity together with genes from a human antibody molecule of appropriate biological activity can be used. Alternatively, techniques described, for example, the production of single chain antibodies (U.S. Pat. No. 4,946,778) can be adapted to produce single chain antibodies specific to one of the binding partners.

Antibody fragments which recognize specific epitopes may be generated by know techniques. For example, such fragments include but are not limited to: the $F(ab^1)_2$ fragments which can be produced by pepsin digestion of the antibody molecule and the Fab fragments which can be generated by reducing the disulfide bridges of the $F(ab^1)_2$ fragments. Alternatively, Fab expression libraries may be constructed according to Science, 246:1275-1281 (1989) to allow rapid and easy identification of monoclonal Fab fragments with the desired specificity.

C. Id-1 and Id-2 Genes, Id-1 and Id-2 Protein—Markers for Detection of and Targets for Treatment Because of their negative correlation and different function in the breast tissue, Id-1 or Id-2 genes, Id-1 or Id-1 mRNAs, or Id-1 or Id-2 proteins may each individually be used as a marker for detection and/or prognosis of malignant aggressivity or as a target for gene therapy.

D. Combination of Id-1 and Id-2 Genes—Marker and Target

Similarly, a ratio of both genes and/expressed proteins may be advantageously used for diagnosis and/or prognosis of breast cancer cells aggressivity.

E. Prognosis of Breast Cancer

In one aspect of the present invention, a method is provided that is useful in the prognosis of breast cancer.

The method for prognosis comprises detecting expression for an Id gene product in breast tissue obtained from a patient, and more preferably by seeking to detect gene products, that is Id-1 and Id-2 proteins or mRNAs. For example, the presence of Id-2 gene product (protein or MRNA) and the absence of Id-1 gene product, or a relatively larger amount of Id-2 with respect to Id-1, is a prognostic indicator that breast cancer cells in the breast tissue will remain localized.

III. A Diagnostic Kit for Detection of Breast and other Types of Cancer Aggressivity The invention further concerns the detection of Id-1, Id-2 or their ratio with a kit comprising anti Id-1 and/or Id-2 antibodies or Id-1 and/or Id-2 probes.

The kit for detection of breast cancer aggressivity is based on a method of using Id-1 and Id-2 antibodies or probes.

The kit typically comprises a detection means for detecting either the Id-1 and/or Id-2 expression product mRNA, or Id-1 and/or Id-2 product. For detection of Id-1 or Id-2 protein, antibodies for Id-1 protein are contacted with breast tissue under conditions allowing the Id-1 antibodies to bind to Id-1 protein, if present. Another sample of the same breast tissue is similarly contacted with antibodies for Id-2 protein under conditions allowing the Id-2 antibodies to bind to Id-2 protein, if present. The presence of bound Id-2 antibodies with the absence of bound Id-1 antibodies is a prognostic indicator that breast cancer cells in the breast tissue are noninvasive and remain localized. The presence of Id-1 antibodies with the absence of Id-2 binding is a prognostic indicator of the presence of aggressive cancer. Quantitating both responses derives a ratio of Id-1/Id-2. The ratio above 1 indicates aggressive cancer. The ratio lower than 1 indicates less aggressive or non-aggressive cancer.

IV. Method for Treatment of Breast Cancer

A method for treatment of breast, endometrial, cervical, ovarian, squamous cells or prostate carcinoma or melanoma comprises targeting of Id-1, or Id-2 genes, or a combination thereof, through delivery of antisense transcripts, ribozymes, cationic liposomes, small therapeutically active molecules, drugs, peptides or organic compounds that disrupt Id-1 interaction with a bHLH transcription factor or enhance Id-2 gene interaction with a bHLH transcription factor and vice versa, RNA, anti-Id-1 RNAi causing degradation of homologous Id-1 mRNAs, Id-2 as a gene or a protein, ITF-2 as a gene or protein, or targeting Id-1 or Id-2 proteins with antibodies or with compounds which either enhance or inhibit their production.

A. Gene Therapy for Treatment

Gene therapy provides a way to manipulate genetic makeup of the cell. There are two general approaches to gene therapy.

The first approach utilizes the introduction into a patient of a vector that inserts into the genetic code a sequence in the case of breast cancer, Id-2 sequence, that replaces the more aggressive Id-1 gene, with the less aggressive Id-2 gene.

The second approach utilizes the genetic code of Id-1 or Id-2 to deliver to the breast cells Id-1 or Id-2 antisense molecules that enter the breast cells and by sequence recognition, selectively inhibit the gene, Id-1 gene in this case, expression.

Both approaches are intended to be within the scope of this invention.

B. Gene Therapy Approaches

A variety of gene therapy approaches may be used in accordance with the invention to modulate expression of the Id-1 or Id-2 gene in vivo. For example, antisense DNA molecules may be engineered and used to block translation of mRNA in vivo.

Alternatively, ribozyme molecules may be designed to cleave and destroy the Id-1 or Id-2 mRNAs in vivo.

In another alternative, oligonucleotides designed to hybridize to the 5' region of the Id-1 or Id-2 gene (including the region upstream of the coding sequence) and form triple helix structures may be used to block or reduce transcription of the Id-1 or Id-2 gene.

In yet another alternative, nucleic acid encoding the full length wild-type Id-1 or Id-2 message may be introduced in vivo into cells which otherwise would be unable to produce the wild-type Id-1 or Id-2 gene product in sufficient quantities or at all.

In a preferred embodiment, the antisense, ribozyme and triple helix nucleotides are designed to inhibit the translation or transcription of Id-1 with minimal effects on the expression of Id-2. In a preferred embodiment, the antisense, ribozyme and triple helix nucleotides are designed to inhibit the translation or transcription of Id-2 with minimal effects on the expression of Id-1. To accomplish this, the oligonucleotides used are designed on the basis of relevant sequences unique to Id-1 or Id-2, i.e., those sequences found in Id-1 but not in Id-2 or Id-2 and not Id-1.

For example, and not by way of limitation, the oligonucleotides should not fall within those regions where the nucleotide sequence of both Id genes is most homologous.

Moreover, the aggressive propensity of Id-1 gene in breast cancer cells may be effectively targeted with Id-1-antisense construct and the aggressive breast cancer cells may be converted to non-aggressive non-invasive cancer cells.

B. Targeting Delivery Vehicles and Products

The current gene delivery methods can be divided to two classes: viral and non-viral.

a. Viral Vectors

The viral vectors currently used both for target validation and gene therapy are mainly of the following types:

1. Adenoviral vectors, mostly Ad2 and Ad5-based recombinant vectors which may or may not contain targeting elements, either via genetic modification or chemical modification of the viral capsid. It can either be a replication-defective virus or a selectively replicating competent virus.

2. Lentivirus vectors with the same modifications as stated for adenoviral vectors.

3. Adeno-associated viral vectors (AAV).

4. Retroviral vectors.

Among these four, the first two are most commonly used for cancer indications.

b. Non-viral Gene Delivery Vehicles

There are several non-viral based gene delivery systems.

1. One class includes physical devices to facilitate uptake including direct injection of plasmid DNA, gene guns, electroporation, microinjection, electrical pulses, and ultrasound.

2. The other class of non-viral based methods more relevant to systemic delivery are the synthetic gene delivery systems that are defined by their use of:

i) cationic lipids, also called cationic liposomes or lipoplexes; Cationic lipids enter the cell by endocytosis and traverse the cytoplasm through various endocytic compartments. In this process, these complexes are either targeted to lysosomes for degradation, or are released into the cytoplasm. One way to deliver gene to its target is by forming cationic liposome-DNA complex which targets gene expression to vascular endothelial cells, macrophages and tumor cells.

In practice, for example, cationic liposome-Id-2-DNA complex is prepared and targeted to carcinoma cells to replace a highly aggressive Id-1 gene with less aggressive Id-2 gene.

ii) polycationic polymers or polyplexes.

3. Another delivery vehicle for targeting of the Id-1 gene is RNA interference (RNAi) process. The RNAi process utilizes a sequence-specific post-transcriptional gene silencing of Id-1 gene by providing a double-stranded RNA (Id-1-dsRNA) that is homologous in sequence to the Id-1 gene. Small interfering RNAs (siRNAs) generated by ribonuclease III cleavage from longer Id-1-dsRNA are the mediators of sequence-specific Id-1-mRNA degradation.

4. Another type of targeting delivery vehicles are recently newly developed nanotechnologies. There are currently two nanotechnologies developed and available for gene transfers and drug delivery, namely dendritic polymers and micellar nanoparticles. Dendritic polymers, also called dendrimers are polymers suitable and useful for the design and assembly of nanoscale materials. Micellar nanoparticles are unique synthetic lipid vesicles that fuse with cell membrane.

Non-viral based gene delivery systems offer ease of preparation, enhanced DNA packaging capacity and low immunogenicity.

In terms of the type of molecules the gene delivery vehicles can deliver, they include plasmids expressing cDNA of the therapeutic genes (ITF-2 or Id-2, for example in the breast) or the actual therapeutic molecules. Additionally, anti-sense expressing plasmids (Id-1 antisense, for example) or the antisense oligonucleotides themselves may be used as a delivery vehicle to target cancer genes. Small molecule inhibitors of Id-1-interacting proteins are also suitable.

The use of antisense DNA and DNA vectors is described, for example, in *Clinical Trials of Genetic Therapy with Antisense DNA and DNA Vectors*, Ed. Eric Wickstrom, Marcel Decker, Inc. (1998), incorporated by reference.

In conclusion, there are different ways to develop cancer therapeutics using helix-loop-helix proteins as targets. These different ways include, but are not limited to, the ones previously described.

VI. Pharmaceutical Formulations and Compositions

Any of the identified compounds, antisense DNA molecules, antibodies, delivery vehicles, etc., can be administered to a mammal, including a human patient, directly, or in pharmaceutical compositions comprising its admixture with suitable carriers or excipient(s) at doses therapeutically effective to treat or ameliorate a breast, cervical, ovarian, endometrium, squamous cells and prostate cancer and melanoma.

A therapeutically effective dose refers to that amount of the composition sufficient to result in treatment or amelioration of symptoms associated with aggressive cancer cells. Various techniques for formulation and administration of the compositions of the instant application may be found in "Remington's Pharmaceutical Sciences," Mack Publishing Co., Easton, Pa., latest edition.

The products of the invention may be designed or administered for tissue specificity. If the compound comprises a nucleic acid molecule, including those comprising an expression vector, it may be linked to a regulatory sequence which is specific for the target tissue, such as the breast tissue, cervix, ovarian, endometrium, squamous cells, prostate or skin, etc., by methods which are know in the art including those set forth in *Ann. Oncol.*, 5 Suppl 4:59-65 (1994); *Gene*, 145:305-310 (1994); *Surgery*, 116:205213 ((1994); *Cancer Res.*, 54:4266-4269; *Cancer*, 74 (Suppl. 3):1021-1025 (1994); *Proc. Nat'l. Acad. Sci. USA*, 91:1460-1464; *Exp. Hematol.*, 22:223-230; *Prog. Clin. Biol. Res.*, 388:361-365 (1994). The compounds of the invention may be targeted to specific sites by direct injection to those sites, such as breast, in the case of breast cancer.

Pharmaceutical compositions suitable for use in the present invention include compositions wherein the active ingredients are contained in an effective amount to achieve its intended purpose. More specifically, a therapeutically effective amount means an amount effective to stop aggressive metastatic cancer growth and to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes the IC50 (the dose where 50% of the cells show the desired effects) as determined in cell culture. Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population).

The dose ratio between toxic and therapeutic effects is the therapeutic index and it can be expressed as the ratio between LD50 and ED50. Compounds which exhibit high therapeutic indices are preferred. The data obtained from the cell culture assays described above and animal studies can be used in formulating a range of dosage for use in humans. The dosage of such compounds lies preferably within a range of circulating concentrations that include the ED50 with little or no toxicity.

The dosage may vary within this range depending upon the dosage form employed and the route of administration utilized. The exact formulation, route of administration and dosage can be chosen by the individual physician in view of the patent's condition. Dosage amount and interval may be adjusted individually to provide plasma levels of the active moiety which are sufficient to maintain the desired effects.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions and a suitable organic solvent or solvent mixture. Dye stuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticiser, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluorethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multidose containers, with the added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions to the active compounds may be prepared as appropriate oily injection suspensions. Suitable lipophilic solvents or vehicles include fatty oils such as a sesame oil, or synthetic fatty acid esters, such as ethyl oleate or triglycerides, liposomes or cationic liposomes. Aqueous injection suspensions may contain substances which increase the viscosity of the suspension, such as sodium carboxymethyl cellulose, sorbitol, or destran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulation described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. Naturally, the proportions of a co-solvent system may be varied considerably without destroying its solubility and toxicity characteristics. Furthermore, the identify of the co-solvent components may be varied.

Alternatively, other delivery systems for hydrophobic pharmaceutical compounds may be employed. Liposomes, particularly cationic liposomes, and emulsions are well known examples of delivery vehicles or carriers for hydrophobic drugs. Certain organic solvents such as dimethylsulfoxide also may be employed although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to, calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to, hydrochloric, sulfuric, acetic, lactic, tartaric, malic, succinic, etc. Salts tend to be more soluble in aqueous or other protonic solvents that are the corresponding free base forms.

Routes of Administration

Suitable routes of administration may, for example, include oral, rectal, transmucosal, transdermal, or intestinal administration, parenteral delivery, including intramuscular, subcutaneous, intravenous, intraperitoneal or intranasal.

Alternatively, one may administer the compound in a local rather than systemic manner, for example, via injection of the compound directly into an affected area, often in a depot or sustained release formulation.

Furthermore, one may administer the drug in a targeted drug delivery system, for example, in a liposome coated with an antibody specific for affected cells. The liposomes will be targeted to and taken up selectively by the cells.

It is to be understood that while the invention has been described above in conjunction with preferred specific embodiments, the description and examples are intended to illustrate and not limit the scope of the invention.

EXAMPLE 1

Production of pBabe-Id-1 Retroviral Vector and Virus

This example describes production of pBabe-Id-1 retroviral vector and virus.

The full-length human Id-1 cDNA was excised from CMV-Id-1 and cloned into pBabe-puro, a gift from Dr. Hartmut Land, ICRF, London, United Kingdom. Clones in which the Id-1 cDNA was inserted in the sense orientation (pBabe-Id-1) were selected for use.

pBabe-Id-1 was transfected into the TSA54 packaging cell line (Cell Genesis; Foster City, Calif.) using calcium phosphate. Twenty-four hours after transfection, culture medium containing infectious virus was harvested twice at 4 hour intervals and was frozen at −80° C. Viral titers were determined by reverse-transcriptase activity. Briefly, thawed aliquots of harvested media were incubated with poly(A) (20 ng/µl), oligo dT (10 ng/µl), and [$^3$H]TTP (0.1µCi/µl) in reaction buffer (50 mM Tris-HCl, 75 mM Kcl, 0.5 mM EGTA, and 5 mM MgCl$_2$) for 30 minutes at 37° C. The reaction mixture was spotted on Whatman DE81 paper, which was washed with 2×SSC and counted in a scintillation counter. One unit of MMLV reverse transcriptase (Life Technologies, Inc.) was subjected to the same reaction, and the amount of incorporated [$^3$H]TTP was defined as 1 RT unit. The retroviral titer (RT units/ml) was determined by comparing the amount of [$^3$]TTP incorporated by the virus-containing medium with that incorporated by MMLV reverse transcriptase.

EXAMPLE 2

Cell Culture and Retroviral Infection

This example describes cell lines, cell culture conditions and retroviral infection.

Human breast cancer cell lines MCF7, T47D, and MDA-MB-231 were purchased from the American Tissue Culture Collection (ATCC). Metastatic MDA-MB-435 cells from ATCC were selected for a highly aggressive phenotype by passage in immunodeficient mice. Briefly, cells were injected into nude mice and fast growing tumors were harvested 3-4 weeks later and processed for in vitro cultivation. Fibroblasts were eliminated from the culture by differential trypsinization, and the tumor cells were expanded and cryopreserved for future use.

Breast cancer cell lines were grown in DMEM or RPMI 1640 obtained from University of California, San Francisco, containing 10% fetal bovine serum and insulin (5 µg/ml, Sigma) . For experiments using serum-free medium, fetal bovine serum was omitted.

Approximately eight RT-units of either pBabe-puro or pBabe-Id-1 retrovirus were mixed with 5 ml of medium containing 4 µg/ml polybrene and were added to T47D cells in 100-mm dishes. Cells expressing the retroviral genes were selected in 0.6 µg/ml puromycin, which killed all of the mock-infected cells within three days, whereas 80 or 30% of the pBabe-puro- or pBabe-Id-1-infected cells, respectively, survived. These puromycin-resistant cells are referred to as T47D-pBO or T47D-Id-1. To establish single-cell clones, the T47D-Id-1 population was plated at 1-2 cells/well in 24-well tissue culture plates. Clones that grew in the wells were expanded.

EXAMPLE 3

RNA Isolation and Northern Analysis

This example describes conditions used for RNA isolation and Northern analysis.

Total cellular RNA was isolated and purified as described in *Anal. Biochem.*, 162:156-159 (1987). Twenty µg were separated by electrophoresis through formaldehyde-agarose gels and transferred to a nylon membrane (Hybond N; Amersham). The membrane was hybridized to a $^{32}$P-labeled human Id-1 cDNA or Id-2 or β-casein probe according to *J. Biol. Chem.*, 269:2139-2145 (1994) and was washed and exposed to XAR-5 film for autoradiography. The same blot was hybridized to a 28S rRNA probe to control for RNA integrity and quantitation.

EXAMPLE 4

Western Analysis

This example describes conditions used for Western analysis of breast cancer cells.

Cells were lysed in 2× Laemmli buffer and stored at −70° C. Protein concentration was determined by the DC protein assay (Bio-Rad, Hercules, Calif.). Samples (20-30 μg) were separated by SDS-PAGE and were transferred to a Immobilin-P filter (Millipore) by standard methods. The membrane was blocked for 1 hour at room temperature with TBST (20 mM Tris Base, 137 mM NaCl, 3.8 mM, HCl, and 0.1% Tween 20) containing 5% nonfat milk, and incubated with a rabbit polyclonal antibody against human Id-1 or Id-2 (C-20; Santa Cruz Biotechnology) or with a rabbit polyclonal antibody specific for the PR-A and PR-B forms of the Pg receptor (C-20; Santa Cruz Biotechnology) for 1.5 hours. The membrane was washed, incubated with secondary antibody (goat antirabbit IgG-horseradish peroxidase; Santa Cruz Biotechnology), washed again, and developed for enhanced chemiluminescence using the Amersham ECL kit, according to the supplier's instructions.

EXAMPLE 5

Boyden Chamber Invasion Assays

This example illustrates conditions used for Boyden Chamber invasion assays.

Invasion assays were performed in modified Boyden chambers with 8 μm pore filter inserts for 24-well plates (Collaborative Research). Filters were coated with 10-12 μl of ice-cold Matrigel (8 mg/ml protein; Collaborative Research). Cells (80,000 per well) were added to the upper chamber in 200 μl of the appropriate medium containing 0.1% BSA. Cells were assayed in triplicate or quadruplicate, and the results were averaged. The lower chamber was filled with 300 μl of NIH-3T3 cell-conditioned medium. After a 20 hour incubation, cells were fixed with 2.5% glutaraldehyde in PBS and were stained with 0.5% toluidine blue in 2% $Na_2CO_3$. Cells that remained in the Matrigel or attached to the upper side of the filter were removed with cotton tips. Cells on the lower side of the filter were counted using light microscopy.

EXAMPLE 6

[$^3$H]-Thymidine-Labeling

This example describes conditions used for labeling cells with [$^3$H]-thymidine.

Cells cultured on coverslips were given [$^3$H]-thymidine (10 μCi/ml; 60-80 Ci/mmol; Amersham) for the last 16 hours of the experiments, unless otherwise indicated, whereupon they were fixed with methanol/acetone (1:1) and stained with DAPI. [$^3$H]-thymidine-labeling was developed as described previously in *Mol. Cell Biol.*, 18:4577-4588 (1988). The percentage of labeled nuclei was calculated by comparing the number of [$^3$H]-thymidine-labeled nuclei with the number of DAPI-stained nuclei in a given field, using phase contrast and fluorescence microscopy.

EXAMPLE 7

Antisense Oligonucleotide Treatment

This example describes conditions used for antisense oligonucleotide treatment of T47D cells.

Phosphorothiolated oligonucleotides were made by Life Technologies, Inc. The Id-1 antisense oligonucleotide and nonspecific control oligonucleotide were described in *J. Biol. Cheml*, 269:2139-2145 (1994). T47D cells were cultured on coverslips in serum-free medium for 2 days. On days 3 and 4, the medium was changed in the morning to serum-free medium containing either E2 (10 nM), or E2 and the oligonucleotides (10 μM). On the evening of day 4, protein was extracted from one set of dishes, whereas [$^3$H]-thymidine was added to the other set for an additional 16 hours. Cells were fixed on day 5 and assessed for labeled nuclei as described above.

EXAMPLE 8

Immunohistochemistry

This example describes conditions used for immunohistochemical treatment of tumor tissue sections.

Formalin-fixed paraffin-embedded tumor tissue sections obtained from the CPMC patient protein expression in both DCIS and infiltrating Grades 1, 2 and 3 ductal carcinomas.

Slides were de-waxed, re-hydrated, and placed in a container containing 1 liter of 0.01 M citrate buffer (pH 6.0); they were then microwaved at 700 W for 20 minutes, allowed to remain in the hot citrate buffer for 15 minutes, and cooled down in running cold water. The slides were washed in deionized water and incubated in 10% nonfat dry milk for 30 minutes at room temperature, washed in TBS, and incubated with 1 μg/ml of anti Id-1 antibody overnight at 40° C. Control slides were incubated with rabbit immunoglobulins. The slides were washed in TBS and incubated with biotinylated swine antirabbit F(ab')$_2$ fragments (I:400) for 30 minutes. After washing in TBS, endogenous peroxidase was visualized by incubating in 0.5 mg/ml diaminobenzidine-4-HCl and 0.03% hydrogen peroxide in TBS for three minutes. The slides were washed in TBS and water before mounting.

EXAMPLE 9

Manipulation of Id-2 Expression in Breast Cells

This example describes methods used for manipulation of Id-2 expression in breast cells.

Id-2 cDNA was digested with XbaI and HindIII to isolate a 1.2 kb fragment. The viral LXSN vector that was used for the mouse Id-2 cDNA has already been digested with EcoRI, blunted with T4 DNA polymerase and dephosphorylated with CIAP. The Id-2 fragment was similarly blunted with T4 DNA polymerase, was inserted inside the dephosphorylated vector, and the ligation product transformed into Top-10 cells. To identify the clones with sense or anti-sense orientation, digestion of the recovered plasmids was performed with either NcoI or BstEII enzymes, and the size of the expected fragments determined on ethidium bromide agarose gels. The viral vectors was then packaged in TSA-54 cells (Cell Genesis; Foster City, Calif.). Mammary epithelial cells were infected with control, Id-2 sense or Id-2 antisense vectors and selected with neomycin. One to two weeks after infection, resistant colonies were pooled and expanded.

EXAMPLE 10

Id-2 Protein Expression in Tumor Biopsies

This example describes studies performed to demonstrate Id-protein expression in tumor biopsies.

Breast samples have been obtained from patients undergoing tumorectomies. In order to maintain the integrity of the tissue, paraffin embedded sections were used instead of frozen sections. Tissues were fixed overnight at 4° C. in PBS, pH 7.2, containing 4% paraformaldehyde, dehydrated by graded alcohol and finally embedded in paraffin.

Id-2 expression is studied in a representative number of in situ and invasive breast tumors. As for Id-1, a sample size of 30 ductal carcinomas in situ as well as 30 invasive Grade I and 30 invasive Grade 3 tumor tissues are used.

A specific rabbit anti-Id-2 antibody obtained from Santa Cruz Biotechnology (C-20) is used for immunohistochemistry experiments. Slides are dewaxed, re-hydrated and placed in a container containing citrate buffer (pH 6.0), microwaved, allowed to remain in the hot citrate buffer for 15 min, and cooled down in running cold water. The slides are washed in deionized water and incubated in 10% non fat dry milk, washed in TBS and incubated with 1 μg/ml of anti Id-2 antibody overnight at 4° C. Control slides are incubated with rabbit immunoglobulin, washed in TBS and incubated with biotinylated swine anti-rabbit F(ab) '2 (1:400). The slides are then washed in TBS and incubated with 1:500 streptavidin-horse radish peroxidase. Peroxidase is visualized by incubating in 0.5 mg/ml diaminobenzidine-4HCl and 0.03% hydrogen peroxide.

It is claimed:

1. A method for prognosis of the propensity of breast cancer metastasis, said method comprising:
   a) obtaining a biopsied breast tissue sample;
   detecting a positive level of Id-1 protein (SEQ ID NO:2) in said biopsied sample as compared to negative Id-1 protein (SEQ ID NO:2) in normal breast cells, whereby the positive level of Id-1 (SEQ ID NO:2) in the biopsied sample as compared to negative Id-1 (SEQ ID NO:2) in normal breast cells serves to indicate breast cancer metastatic propensity.

2. The method of claim 1 wherein the Id-1 protein (SEQ ID NO:2) is detected with Id-1 antibodies.

3. The method of claim 1 wherein the Id-1 protein (SEQ ID NO:2) is detected with immunohistochemical analysis.

4. A method for prognosis of the propensity of breast cancer metastasis, said method comprising:
   a) providing an anti- Id-1 protein antibody;
   b) contacting the anti- Id-1 antibody with a sample of biopsied breast tissue under conditions permitting said antibody to bind to the Id-1 protein (SEQ ID NO: 2);
   c) detecting the binding of the anti- Id-1 antibody to the Id-1 protein (SEQ ID NO: 2) by formation of the Id-1 protein/antibody complex; and
   detecting a positive level of Id-1 protein (SEQ ID NO:2) in said biopsied sample as compared to negative Id-1 protein (SEQ ID NO:2) in normal breast cells, whereby the positive level of Id-1 protein (SEQ ID NO:2) in the biopsied sample as compared to negative Id-1 protein (SEQ ID NO:2) in normal breast cells serves to indicate breast cancer metastatic propensity.

5. The method as in claim 4 wherein the formation of the complex is determined by visual examination.

* * * * *

SEQUENCE LISTING

<160> NUMBER OF SEQ ID NOS: 4

<210> SEQ ID NO 1
<211> LENGTH: 926
<212> TYPE: DNA
<213> ORGANISM: Homo sapiens

<400> SEQUENCE: 1

```
ggggcccatt ctgtttcagc cagtcgccaa gaatcatgaa agtcgccagt ggcagcaccg      60
ccaccgccgc cgcgggcccc agctgcgcgc tgaaggccgg caagacagcg agcggtgcgg     120
gcgaggtggt gcgctgtctg tctgagcaga gcgtggccat ctcgcgctgc cggggcgccg     180
gggcgcgcct gcctgccctg ctggacgagc agcaggtaaa cgtgctgctc tacgacatga     240
acggctgtta ctcacgcctc aaggagctgg tgcccaccct gccccagaac cgcaaggtga     300
gcaaggtgga gattctccag cacgtcatcg actacatcag ggaccttcag ttggagctga     360
actcggaatc cgaagttggg acccccgggg gccgagggct gccggtccgg gctccgctca     420
gcaccctcaa cggcgagatc agcgccctga cggccgaggc ggcatgcgtt cctgcggacg     480
atcgcatctt gtgtcgctga agcgcctccc ccagggaccg gcggacccca gccatccagg     540
gggcaagagg aattacgtgc tctgtgggtc tcccccaacg cgcctcgccg gatctgaggg     600
agaacaagac cgatcggcgg ccactgcgcc cttaactgca tccagcctgg ggctgaggct     660
gaggcactgg cgaggagagg gcgctcctct ctgcacacct actagtcacc agagacttta     720
gggggtggga ttccactcgt gtgtttctat tttttgaaaa gcagacattt taaaaaatgg     780
tcacgtttgg tgcttctcag atttctgagg aaattgcttt gtattgtata ttacaatgat     840
caccgactga gaatattgtt ttacaatagt tctgtggggc tgttttttg ttattaaaca     900 aataatttag atggtgaaaa aaaaaa                                          926
```

<210> SEQ ID NO 2
<211> LENGTH: 154
<212> TYPE: PRT
<213> ORGANISM: Homo sapiens

<400> SEQUENCE: 2

```
Met Lys Val Ala Ser Gly Ser Thr Ala Thr Ala Ala Gly Pro Ser
1               5                   10                  15

Cys Ala Leu Lys Ala Gly Lys Thr Ala Ser Gly Ala Gly Glu Val Val
                20                  25                  30

Arg Cys Leu Ser Glu Gln Ser Val Ala Ile Ser Arg Cys Arg Gly Ala
            35                  40                  45

Gly Ala Arg Leu Pro Ala Leu Leu Asp Glu Gln Gln Val Asn Val Leu
        50                  55                  60
```

Leu Tyr Asp Met Asn Gly Cys Tyr Ser Arg Leu Lys Glu Leu Val Pro
65                  70                  75                  80

Thr Leu Pro Gln Asn Arg Lys Val Ser Lys Val Glu Ile Leu Gln His
            85                  90                  95

Val Ile Asp Tyr Ile Arg Asp Leu Gln Leu Glu Leu Asn Ser Glu Ser
            100                 105                 110

Glu Val Gly Thr Pro Gly Gly Arg Gly Leu Pro Val Arg Ala Pro Leu
        115                 120                 125

Ser Thr Leu Asn Gly Glu Ile Ser Ala Leu Thr Ala Glu Ala Ala Cys
    130                 135                 140

Val Pro Ala Asp Asp Arg Ile Leu Cys Arg
145                 150

<210> SEQ ID NO 3
<211> LENGTH: 1049
<212> TYPE: DNA
<213> ORGANISM: Homo sapiens

<400> SEQUENCE: 3
gcccggtgcc aagcgcagct agctcagcag gcggcagcgg cggcctgagc ttcagggcag      60
ccagctcctc ccgtctcgc cttcctcgcg gtcagcatga aagccttcag tcccgtgagg     120
tccgttagga aaacagcct gtcggaccac agcctgggca tctcccggag caaaaccct     180
gtggacgacc cgatgagcct gctatacaac atgaacgact gctactccaa gctcaaggag     240
ctggtgccca gcatccccca gaacaagaag gtgagcaaga tggaaatcct gcagcacgtc     300
atcgactaca tcttggacct gcagatcgcc ctggactcgc atcccactat tgtcagcctg     360
catcaccaga gacccgggca gaaccaggcg tccaggacgc cgctgaccac cctcaacacg     420
gatatcagca tcctgtcctt gcaggcttct gaattcccct ctgagttaat gtcaaatgac     480
agcaaagcac tgtgtggctg aataagcggt gttcatgatt tcttttattc tttgcacaac     540
aacaacaaca acaaattcac ggaatctttt aagtgctgaa cttatttttc aaccatttca     600
caaggaggac aagttgaatg dacctttta aaaagaaaaa aaaatgaag gaaaactaag     660
aatgatcatc ttcccagggt tcttacttga ctgtaattcg ttatttatga aaaacctttt     720
taaatgccct ttctgcagtt ggaaggtttt ctttatatac tattcccacc atggggagcg     780
aaaacgttaa atcacaagg aattgcccaa tctaagcaga ctttgccttt tttcaaaggt     840
ggagcgtgat accagaagga tccagtattc agtcacttaa atgaagtctt ttggtcagaa     900
attaccttt tcacacaagc ctactgaatg ctgtgtatat atttatatat aaatatatct     960
atttgagtga aaccttgtga acctttaatt agagtcttct tgtatagtgg cagagatgtc    1020
tattctgcat caaagtgtaa tgatgtact                                      1049

<210> SEQ ID NO 4
<211> LENGTH: 134
<212> TYPE: PRT
<213> ORGANISM: Homo sapiens

<400> SEQUENCE: 4

Met Lys Ala Phe Ser Pro Val Arg Ser Val Arg Lys Asn Ser Leu Ser
1               5                   10                  15

Asp His Ser Leu Gly Ile Ser Arg Ser Lys Thr Pro Val Asp Asp Pro
            20                  25                  30

Met Ser Leu Leu Tyr Asn Met Asn Asp Cys Tyr Ser Lys Leu Lys Glu
        35                  40                  45

-continued

```
Leu Val Pro Ser Ile Pro Gln Asn Lys Lys Val Ser Lys Met Glu Ile
    50                  55                  60

Leu Gln His Val Ile Asp Tyr Ile Leu Asp Leu Gln Ile Ala Leu Asp
65                  70                  75                  80

Ser His Pro Thr Ile Val Ser Leu His His Gln Arg Pro Gly Gln Asn
                85                  90                  95

Gln Ala Ser Arg Thr Pro Leu Thr Thr Leu Asn Thr Asp Ile Ser Ile
            100                 105                 110

Leu Ser Leu Gln Ala Ser Glu Phe Pro Ser Glu Leu Met Ser Asn Asp
        115                 120                 125

Ser Lys Ala Leu Cys Gly
        130
```